US006376521B1

(12) United States Patent
Jacobson et al.

(10) Patent No.: US 6,376,521 B1
(45) Date of Patent: Apr. 23, 2002

(54) A3 ADENOSINE RECEPTOR ANTAGONISTS

(75) Inventors: Kenneth A. Jacobson, Silver Spring; An-Hu Li, Bethesda, both of MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/743,412

(22) PCT Filed: Jul. 2, 1999

(86) PCT No.: PCT/US99/15562

§ 371 Date: Apr. 2, 2001

§ 102(e) Date: Apr. 2, 2001

(87) PCT Pub. No.: WO00/02861

PCT Pub. Date: Jan. 20, 2000

Related U.S. Application Data

(60) Provisional application No. 60/092,292, filed on Jul. 10, 1998.

(51) Int. Cl.$^7$ ...................... A61K 31/44; A61K 31/455; C07D 213/80; C07D 211/190
(52) U.S. Cl. ...................... 514/356; 546/322; 546/321; 546/318
(58) Field of Search .......................... 514/356; 546/322, 546/321, 318

(56) References Cited

U.S. PATENT DOCUMENTS

| | | |
|---|---|---|
| 4,048,171 A | 9/1977 | Bossert et al. |
| 4,548,818 A | 10/1985 | Kjellin et al. |
| 4,659,717 A | 4/1987 | Wikel |
| 4,672,068 A | 6/1987 | Kutsuma et al. |
| 4,772,607 A | 9/1988 | Badger et al. |
| 4,866,072 A | 9/1989 | Edwards et al. |
| 5,032,593 A | 7/1991 | Rzeszotarski et al. |
| 5,096,916 A | 3/1992 | Skupin |
| 5,140,015 A | 8/1992 | Olsson et al. |
| 5,310,731 A | 5/1994 | Olsson et al. |
| 5,366,977 A | 11/1994 | Pollard et al. |
| 5,443,836 A | 8/1995 | Downey et al. |
| 5,688,774 A | 11/1997 | Jacobson et al. |
| 5,773,423 A | 6/1998 | Jacobson et al. |
| 5,877,179 A | 3/1999 | Pollard et al. |
| 6,066,642 A | 5/2000 | Jacobson et al. |

FOREIGN PATENT DOCUMENTS

| | | |
|---|---|---|
| DE | 4325254 | 7/1993 |
| EP | 0 217 530 | 4/1987 |
| EP | 374808 | 6/1990 |
| EP | 0 374 808 | 6/1990 |
| WO | WO 94/03456 | 2/1994 |
| WO | WO 94/25605 | 11/1994 |
| WO | WO 94/25607 | 11/1994 |
| WO | WO 96/02553 | 2/1996 |
| WO | WO 96/16084 | 5/1996 |
| WO | WO 97/27177 | 7/1997 |

OTHER PUBLICATIONS

Beach et al., *American Journal of Phsiology*, vol. 263, No. 3, Sep. 1992.
Alzheimer et al., *Neuro–Science Letters*, vol. 99 (1989) 107–112.
Bruns et al., *Olecular Pharmacology*, 29, 331–346.
Jacobson et al., *Journal of Medicinal Chemistry*, vol. 35, No. 3, 1992, 407–422.
Arzneim–Forsch, vol. 22, p. 33 (1976).
Jacobson et al., *Biochemistry*, 34, 1995, 9088–9094.
Brackett et al., *Biochemical Pharmacology*, vol. 39, No. 12, 1990, 1897–1904.
Daly, "Mechanism of Action of Caffeine", in *Caffeine, Coffee and Health*, (S. Garattini, Ed.), Chapter 4, pp. 97–150 (1993).
Bruns, *Nucleosides & Nucleotides*, 10, 931–943 (1991).
Bruns et al., *Proc. Nat. Acad. Sci. U.S.A.*, 77, 5547–5551 (1980).
Jacobson et al., "Development of Selective Purinoceptor Agonists and Antagonists", in *Purinergic Approaches In Experimental Therapeutics*, K. A. Jacobson and M.F. Jarvis, Ed., Wiley, Ch. 6, pp. 101–128 (1997).
Zhou et al., *Proc. Natl. Acad. Sci. USA*, 89, 7432–7436 (1992).
Ramkumar et al., *J. Biol. Chem.*, 276, 837–845 (1996) (2 page Abstract).
Von Lubitz et al., *Eur. J. Pharmacol.*, 263, 59–67 1994).
van Rhee et al., *J. Med. Chem.*, 39, 2980–2989 (1996).
Jiang et al., *J. Med. Chem.*, 39, 4667–4675 (1996).
Jiang et al., *J. Med. Chem.*, 40, 2596–2608 (1997).

(List continued on next page.)

Primary Examiner—C. S. Aulakh
(74) Attorney, Agent, or Firm—Leydig, Voit, & Mayer, Ltd.

(57) ABSTRACT

Disclosed are pyridine and dihydropyridine derivatives, pharmaceutical compositions comprising one or more of these derivatives, and a method of selectively blocking an $A_3$ adenosine receptor of a mammal by the use of one or more of these derivatives. An example of the pyridine derivative is of the formula (I):

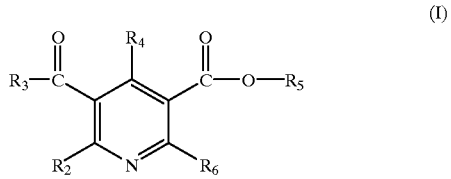

(I)

wherein $R_2$ is ethyl, $R_3$ is ethylsulfanyl; $R_4$ is ethyl, propyl, or hydroxypropyl; $R_5$ is ethyl, propyl, fluoroethyl, or fluoropropyl; and $R_6$ is phenyl or fluorophenyl. The derivatives of the present invention can be used for inhibiting binding of ligands to an adenosine receptor. The derivatives also can be used for characterizing an adenosine receptor.

40 Claims, 17 Drawing Sheets

OTHER PUBLICATIONS

Kim et al., *J. Med. Chem.*, 39, 4142–4148 (1996).

Karton et al., *J. Med. Chem.*, 39, 2293–2301 (1996).

Li et al., *J. Med. Chem.*, 41, 3186–3201 (1998).

Ji et al., "Flavonoid Derivatives as $A_3$ Adenosine Receptor Antagonists", *Abstract from Purines '96*.

van Rhee et al., "Development of 1,4–Dihydropyridines as Selective $A_3$ Adenosine Receptor Antagonists", *Abstract From Purines '96*.

Jacobson et al., "Novel Selective Non–Xanthine $A_3$ Adenosine Receptor Antagonists" *Abstract from Purines '96*.

Volpini et al., "Potent and Selective Adenotine Agonist: 2' and 3'–Deoxy Derivatives of 5'–N–Methycarboxamidoadenosine (MECA)", *Abstract From Purines '96*.

Bergen et al., "$A_3$ Receptors: Structure–Activity Relationships and Molecular Modeling", Abstract of American Chemical Society Meeting, Chicago, Illinois, Aug. 25, 1993.

Ji et al., "Species Differences in Ligand Affinity at Central $A_3$–Adenosine Receptors", Drug Development Research 33:00–00 (1994).

Fozard et al., "Adenosine $A_3$ Receptors mediate Hypotension in the Angiotensin II–support Circulation of the Pithed Rat", Br. J. Pharmacol. 109, 1993, pp 3–5.

Austin et al., "Differential Distribution of $A_3$ Receptor in Rat Brain", Society for Neuroscience Abstracts, vol. 19, 42.11, 1993.

Jacobson et al., "Synthesis and Biological Activity of $N^6$–(p–Sulfophenyl)alkyl and $N^6$–Sulfoalkyl Derivatives of Adenosine: Water–Soluble and Peripherally Selective Adenosine Agonists", Journal of Medicinal Chemistry, vol. 35, No. 22, 1992, pp. 4143–4149.

Carruthers et al., "Adenosine $A_3$ receptors: two into one won't go", Reprinted from Trends in Pharmacological Sciences, vol. 14, No. 8, pp. 290–291, Aug. 1993.

Galen et al., "Xanthine–7–Ribosides as Adenosine Receptor Antagonists: Further Evidence for Adenosine's Anti Mode of Binding", Nucleosides & Nucleotides, 10(5), pp. 1191–1193 (1991).

Jacobson et al., "8–(3–Chlorostyryl)caffeine (CSC) in a selective $A_2$–adenosine antagonist in vitro and in vivo", FEBS Letters, vol. 323, No. 1,2, pp. 141–144, May 1993.

Von Lubitz et al., "Reduction of postischemic brain damage and memory deficits following treatment with the selective adenosine $A_1$ receptor agonist", European Journal of Pharmacology 54886 (1996), pp. 1–6.

Kenneth A. Jacobson, "Adenosine ($P_1$) and ATP ($P_2$) Receptors", John Crerar Lib./UofC, 12.10, pp. 601–642.

Eidelman et al., "$A_1$ adenosine–receptor antagonists activate chloride efflux from cystic fibrosis cells", Proc. Natl. Acad. Sci. USA, vol. 89, pp. 5562–5566, Jun. 1992.

Ward et al., "Intracellular Processing and Degradation of Mutant and Wild–type CFTR", $48^{TH}$ Annual Meeting —Society of General Physiologists, p. 33a.

34-41, 44, 46, 48, 55
pyridine derivatives

THF, reflux, overnight 60-67, 71, 72, 74-76
1,4-dihydropyridines

A3 ADENOSINE RECEPTOR ANTAGONISTS

This application is a 371 of PCT/US99/15562 filed Jul. 2, 1999, now WO 00/02851, which claims the benefit of Ser. No. 60/092,292 filed Jul. 10, 1998.

TECHNICAL FIELD OF THE INVENTION

The present invention relates to certain novel $A_3$ adenosine receptor antagonists, pharmaceutical compositions, and methods of selectively blocking $A_3$ adenosine receptors in a mammal. The present invention also relates to methods of preventing or treating various medical disorders or conditions with the adenosine receptor antagonists.

BACKGROUND OF THE INVENTION

The use of caffeine and other alkylxanthines as physiological stimulants is well known. The principle mechanism by which caffeine and other alkylxanthines act as physiological stimulants is by blocking the effects of the ubiquitous neuromodulator adenosine. Daly, "Mechanism of Action of Caffeine", in *Caffeine, Coffee and Health*, (S. Garattini, Ed.), Chapter 4, pp. 97–150 (1993). Adenosine is produced locally in response to increased activity or stress to the system. This feedback mechanism allows the organ to compensate for the stress by decreasing energy demand (depressant activity) and increasing oxygen supply (e.g., by vasodilation). Bruns, *Nucleosides & Nucleotides*, 10, 931–944 (1991).

Adenosine plays several key physiological roles. In addition to its role in intermediary metabolism, adenosine displays a number of receptor-mediated physiological actions, including dilation of coronary vessels, inhibition of platelet aggregation, and inhibition of lipolysis. Bruns et al., *Proc. Nat. Acad. Sci. U.S.A.*, 77, 5547–5551 (1980). Adenosine receptors, $A_1$, $A_2$, and $A_3$, belong to the G protein-coupled superfamily characterized by seven transmembrane helical domains. Several antagonists have been reported for these receptors in the literature. See, for example, Jacobson et al., "Development Of Selective Purinoceptor Agonists And Antagonists", in *Purinergic Approaches In Experimental Therapeutics*, K. A. Jacobson and M. F. Jarvis, Ed, Wiley, Ch. 6, pp. 101–128 (1997). The pharmacology of the $A_3$ receptor is unique within the class of adenosine receptors. Zhou et al., *Proc. Natl. Acad. Sci. USA*, 89, 7432–7436 (1992).

The distribution of the $A_3$ receptor is found primarily in the central nervous system (CNS), brain, testes, and immune system, where it appears to be involved in the modulation of release from mast cells of mediators of the immediate hypersensitivity reaction. Ramkumar et al., *J. Biol. Chem.*, 268, 16887–16890 (1993). It is believed that $A_3$-selective compounds will have utility in the therapeutic and/or prophylactic treatment of cardiac disease, infertility, kidney disease, and CNS disorders. Activation of the $A_3$ receptor has been linked to several second messenger systems such as stimulation of phospholipidases C and D and inhibition of adenylyl cyclase. Ali et al., *J. Pharmacol. Exp. Therap.*, 276, 837–845 (1996).

Antagonists for the $A_3$ receptor are sought as potential anti-inflammatory, antiasthmatic, and antiischemic agents. von Lubitz et al., *Eur. J. Pharmacol.*, 263, 59–67 (1994); *Soc. For Neurosciences*, Abstr. 745.16, 23, 1924 (1997). Some promising leads for $A_3$ adenosine receptor antagonists have been identified in certain 1,4-dihydropyridines, triazoloquinazolines, flavonoids, a triazolonaphthyridine, and a thiazolopyrimidine. Van Rhee et al., *J. Med. Chem.*, 39, 2980–2989 (1996); Jiang et al., *J. Med. Chem.*, 39, 4667–4675 (1996); Jiang et al., *J. Med. Chem.*, 40, 2596–2608 (1997); Kim et al., *J. Med. Chem.*, 39, 4142–4148 (1996); Karton et al., *J. Med. Chem.*, 39, 2293–2301 (1996); Jacobson et al., *Drug Devel. Res.*, 37, 131 (1996). WO 97/27177 discloses certain dihydropyrdines, pyridines, flavonoids, and triazoloquinazolines as possible $A_3$ adenosine receptor antagonists. Li et al., *J. Med. Chem.*, 41, 3186–3201 (1998) discloses certain pyridine derivatives as possible $A_3$ adenosine receptor antagonists.

Thus, there remains a need for antagonists for $A_3$ adenosine receptors. The present invention seeks to provide such compounds, as well as methods of using these compounds to selectively block adenosine receptors in mammals, and pharmaceutical compositions comprising such compounds. These and other objects and advantages of the present invention, as well as additional inventive features, will be apparent from the description of the invention provided herein.

SUMMARY OF THE INVENTION

The present invention provides compounds of formula (I)

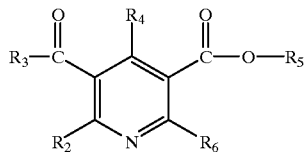

(I)

wherein $R_2$ is selected from the group consisting of $C_1-C_6$ alkyl, $C_3-C_7$ cycloalkyl, and $C_1-C_6$ alkoxy $C_1-C_6$ alkyl; $R_3$ is selected from the group consisting of $C_1-C_6$ alkoxy, $C_1-C_6$ alkylsulfanyl, hydroxy, $C_1-C_6$ alkoxy $C_1-C_6$ alkylsulfanyl, hydroxy $C_1-C_6$ alkylsulfanyl, and halo $C_1-C_6$ alkylsulfanyl, or $R_3$ together with $R_4$ forms a 3–7 membered heterocyclic ring containing O, N, or S; $R_4$ is selected from the group consisting of $C_1-C_6$ alkyl, halo $C_1-C_6$ alkyl, hydroxy $C_1-C_6$ alkyl, $C_1-C_6$ alkoxy, $C_1-C_6$alkylsulfanyl, $C_1-C_6$ alkylamino, $C_1-C_6$ alkylcarbonyl sulfanyl $C_1-C_6$ alkyl, aryl $C_2-C_6$ alkenyl, aryl $C_2-C_6$ alkynyl, formyl, and acetal; $R_5$ is selected from the group consisting of $C_1-C_6$ alkyl, aryl $C_1-C_6$ alkyl, hydroxy $C_1-C_6$ alkyl, and halo $C_1-C_6$ alkyl; and $R_6$ is selected from the group consisting of aryl, $C_3-C_7$ cycloalkyl, and haloaryl; wherein the aryl is a phenyl or naphthyl; or a pharmaceutically acceptable salt thereof.

The present invention further provides compounds of formula (II)

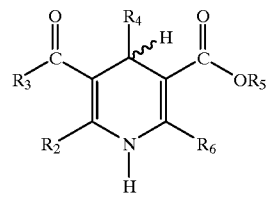

(II)

wherein $R_2$ is a $C_1-C_6$ alkyl; $R_3$ is selected from the group consisting of $C_1-C_6$ alkoxy, $C_1-C_6$ alkoxy $C_1-C_6$ alkylsulfanyl, and $C_1-C_6$ alkylsulfanyl; $R_4$ is selected from the group consisting of $C_1-C_6$ alkyl, acetal, formyl, aryl $C_2$–$C_6$ alkenyl, and aryl $C_2$–$C_6$ alkynyl; $R_5$ is selected from the group consisting of $C_1$–$C_6$ alkyl and aryl $C_1$–$C_6$ alkyl; and $R_6$ is selected from the group consisting of aryl and $C_3$–$C_6$ cycloalkyl; wherein said aryl is a phenyl or naphthyl; or a pharmaceutically acceptable salt thereof.

The present invention further provides pharmaceutical compositions comprising any of the aforesaid compounds and a method of treating a mammal comprising selectively blocking one or more of the adenosine receptors, particularly the $A_3$ adenosine receptors, of the mammal by administering to the mammal at least one compound of formulas I and II.

The present invention further provides a method of characterizing an adenosine receptor, particularly an $A_3$ receptor, in a substrate comprising contacting said substrate with a compound of the present invention and evaluating the interaction of the compound with the adenosine receptor.

The present invention further provides a method of inhibiting the binding of a ligand to an adenosine receptor, particularly an $A_3$ receptor, of a substrate comprising contacting the substrate with a compound of the present invention so that the compound binds to the adenosine receptor and inhibits the ligand from binding to the adenosine receptor.

DETAILED DESCRIPTION OF THE PREFERRED EMBODIMENTS

Figure 1:
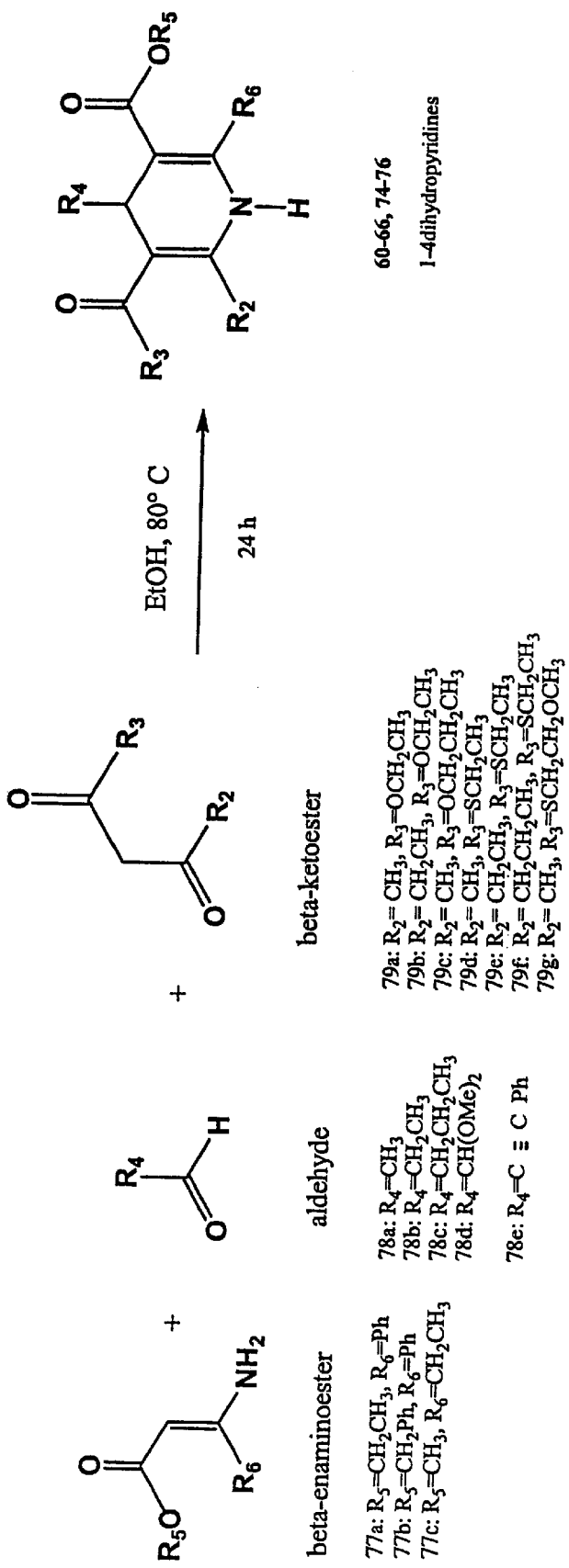
FIG. 1 depicts a method of synthesis of dihydropyridine derivatives 60–66. and 74–76, starting from a β-enaminoester (77a–c), an aldehyde (78a–e), and a β-ketoester (79a–g).
Figure 2:
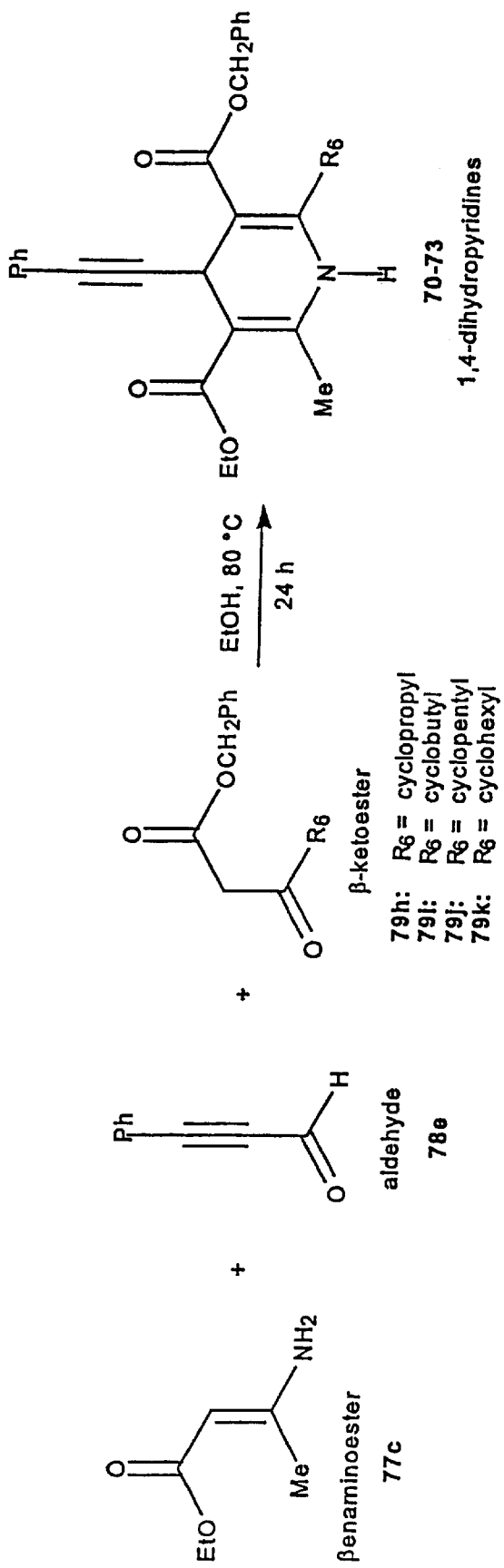
FIG. 2 depicts a method of synthesis of dihydropyridine derivatives 70–73, starting from a β-enaminoester (77c), an aldehyde (78e), and a β-ketoester (79h–k).

The present invention may be best understood with reference to the accompanying drawings and to the following detailed description of the preferred embodiments. The present invention provides compounds of formula (I)

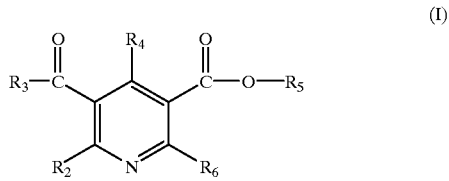

(I)

wherein $R_2$ is selected from the group consisting of $C_1$–$C_6$ alkyl, $C_3$–$C_7$ cycloalkyl, and $C_1$–$C_6$ alkoxy $C_1$–$C_6$ alkyl; $R_3$ is selected from the group consisting of $C_1$–$C_6$ alkoxy, $C_1$–$C_6$ alkylsulfanyl, hydroxy, $C_1$–$C_6$ alkoxy $C_1$–$C_6$ alkylsulfanyl, hydroxy $C_1$–$C_6$ alkylsulfanyl, and halo $C_1$–$C_6$ alkylsulfanyl, or $R_3$ together with $R_4$ forms a 3–7 membered heterocyclic ring containing O, N, or S; $R_4$ is selected from the group consisting of $C_1$–$C_6$ alkyl, halo $C_1$–$C_6$ alkyl, hydroxy $C_1$–$C_6$ alkyl, $C_1$–$C_6$ alkoxy, $C_1$–$C_6$ alkysulfanyl, $C_1$–$C_6$ alkylamino, $C_1$–$C_6$ alkylcarbonyl sulfanyl $C_1$–$C_6$ alkyl, aryl $C_2$–$C_6$ alkenyl, aryl $C_2$–$C_6$ alkynyl, formyl, and acetal; $R_5$ is selected from the group consisting of $C_1$–$C_6$ alkyl, aryl $C_1$–$C_6$ alkyl, hydroxy $C_1$–$C_6$ alkyl, and halo $C_1$–$C_6$ alkyl; and $R_6$ is selected from the group consisting of aryl, $C_3$–$C_7$ cycloalkyl, and haloaryl; wherein the aryl is a phenyl or naphthyl. The nitrogen atom of the heterocyclic ring can be saturated or unsaturated: Thus, for example, the heterocyclic ring can contain an NH group or an NR group wherein R is a $C_1$–$C_6$ alkyl, aryl, formyl, or $C_1$–$C_6$ acyl.

Among the compounds of formula (I), preferred embodiments include those wherein $R_2$ is selected from the group consisting of $C_1$–$C_6$ alkyl, $C_3$–$C_7$ cycloalkyl, and $C_1$–$C_6$ alkoxy $C_1$–$C_6$ alkyl; $R_3$ is selected from the group consisting of $C_1$–$C_6$ alkylsulfanyl, hydroxy, $C_1$–$C_6$ alkoxy $C_1$–$C_6$ alkylsulfanyl, hydroxy $C_1$–$C_6$ alkylsulfanyl, and halo $C_1$–$C_6$ alkylsulfanyl, or $R_3$ together with $R_4$ forms a 3–7 membered heterocyclic ring containing O, N, or S; $R_4$ is selected from the group consisting of $C_1$–$C_6$ alkyl, halo $C_1$–$C_6$ alkyl, hydroxy $C_1$–$C_6$ alkyl, $C_1$–$C_6$ alkoxy, $C_1$–$C_6$ alkylsulfanyl, $C_1$–$C_6$ alkylamino, $C_1$–$C_6$ alkylcarbonyl sulfanyl $C_1$–$C_6$ alkyl, aryl $C_2$–$C_6$ alkenyl, aryl $C_2$–$C_6$ alkynyl, formyl and acetal; $R_5$ is selected from the group consisting of $C_1$–$C_6$ alkyl, aryl $C_1$–$C_6$ alkyl, hydroxy $C_1$–$C_6$ alkyl and halo $C_1$–$C_6$ alkyl; and $R_6$ is selected from the group consisting of aryl, $C_3$–$C_7$ cycloalkyl and haloaryl; wherein the aryl is a phenyl or naphthyl.

Further preferred embodiments the compounds of formula (I) include those wherein $R_2$ is selected from the group consisting of $C_1$–$C_4$ alkyl, $C_4$–$C_5$ cycloalkyl, and $C_1$–$C_3$ alkoxy $C_1$–$C_3$ alkyl; $R_3$ is selected from the group consisting of $C_1$–$C_6$ alkylsulfanyl, hydroxy $C_1$–$C_3$ alkylsulfanyl and halo $C_1$–$C_3$ alkylsulfanyl; $R_4$ is selected from the group consisting of $C_1$–$C_3$ alkyl and hydroxy $C_1$–$C_3$ alkyl; $R_5$ is selected from the group consisting of $C_1$–$C_3$ alkyl and halo $C_1$–$C_3$ alkyl; and $R_6$ is selected from the group consisting of $C_4$–$C_6$ cycloalkyl, phenyl, and halophenyl. Particular embodiments of preferred compounds include those wherein $R_2$ is ethyl; $R_3$ is selected from the group consisting of $C_1$–$C_6$ alkylsulfanyl, hydroxy $C_1$–$C_2$ alkylsulfanyl, and halo $C_1$–$C_2$ alkylsulfanyl; $R_4$ is selected from the group consisting of $C_1$–$C_3$ alkyl and hydroxy $C_1$–$C_3$ alkyl; $R_5$ is selected from the group consisting of $C_1$–$C_3$ alkyl and halo $C_1$–$C_3$ alkyl; and $R_6$ is selected from the group consisting of phenyl and chlorophenyl.

Other embodiments of preferred compounds of formula (I) include those wherein $R_2$ is ethyl; $R_3$ is selected from the group consisting of ethylsulfanyl, hexylsulfanyl, haloethylsulfanyl, and hydroxyethyl sulfanyl; $R_4$ is selected from the group consisting of ethyl, propyl, and hydroxypropyl; $R_5$ is selected from the group consisting of ethyl, propyl, fluoroethyl, and fluoropropyl; and $R_6$ is selected from the group consisting of phenyl and halophenyl. Certain specific embodiments of preferred compounds include those wherein $R_2$ is ethyl; $R_3$ is ethylsulfanyl; $R_4$ is selected from the group consisting of ethyl, propyl, and hydroxypropyl; $R_5$ is selected from the group consisting of ethyl, propyl, fluoroethyl, and fluoropropyl; and $R_6$ is phenyl or fluorophenyl.

Some specific examples of preferred compounds of formula (I) include 5-ethyl 2,4-diethyl 3-(ethylsulfanylcarbonyl)-6-phenylpyridine-5-carboxylate, 5-(2-fluoroethyl)-2,4diethyl-3-(ethysulfanylcarbonyl)-6-phenylpyrdine-5-carboxylate, 5-n-propyl 2,4-diethyl-3-(ethylsulfanylcaronyl)-6-phenylpyridine-5-carboxylate, 5-n-propyl 2-ethyl-4-n-propyl-3-(ethylsulfanylcarbonyl)-6-phenylpyridine-5-carboxylate, 5-n-propyl-2-ethyl-4-(3-hydroxy-n-propyl)-3(ethylsulfanylcarbonyl)-6-phenylpyridine-5-carboxylate, 5-(3-fluoro-n-propyl) 2-ethyl-4-n-propyl-3-(ethylsulfanylcarbonyl)-6-phenylpyridine-5-carboxylate, 5-n-propyl 2-ethyl-4-n-propyl-3-(ethylsulfanylcarbonyl)-6-(2-fluorophenyl) pyridine-5-carboxylate, 5-n-propyl 2-ethyl-4-n-propyl-3-(ethylsulfanylcarbonyl)-6-(3-fluorophenyl)pyridine-5-carboxylate, and 5-n-propyl 2-ethyl-4-n-propyl-3-(ethylsulfanylcarbonyl)-6-(4-fluorophenyl)pyridine-5-carboxylate.

Additional embodiments of preferred compounds of formula (I) include those wherein $R_2$ is ethyl; $R_3$ is selected from the group consisting of hexylsulfanyl, haloethylsulfanyl and hydroxyethylsulfanyl; $R_4$ is selected from the group consisting of ethyl and propyl; $R_5$ is propyl; and $R_6$ is phenyl. Thus, examples of such compounds include 5-n-propyl 2,4-diethyl-3-(n-hexylsulfanylcarbonyl)-6-phenylpyridine-5-carboxylate, 5-n-propyl 2-ethyl-4-n-propyl-3-(2-hydroxyethylsulfanylcarbonyl)-6-phenylpyridine-5-carboxylate, 5-n-propyl 2-ethyl-4n-propyl-3-(2-fluoroethylsulfanylcarbonyl)-6-phenylpyridine-5-carboxylate, and 5-n-propyl 2-ethyl-4-n-propyl-3-(2,2,2-trifluoroethylsulfanylcarbonyl)-6-phenylpyridine-5-carboxylate.

Further embodiments of preferred compounds of formula (I) include those wherein $R_2$ is methyl; $R_3$ is selected from the group consisting of $C_1$–$C_3$ alkoxy, ethylsulfanyl, and methoxyethylsulfanyl; $R_4$ is selected from the group consisting of $C_1$–$C_3$ alkyl and phenylethynyl; $R_5$ is selected from the group consisting ethyl and benzyl; and $R_6$ is selected from the group consisting of phenyl and $C_4$–$C_5$ cycloalkyl. Thus, examples of such preferred compounds include 3-n-propyl 5-ethyl-2,4-dimethyl-6-phenylpyridine-3,5-dicarboxylate, 3,5-diethyl 2-methyl-4-ethyl-6-phenylpyridine-3,5-dicarboxylate, 5-ethyl 2-methyl-4ethyl-3-(ethylsulfanylcarbonyl)-6-phenylpyridine-5-carboxylate, 5-ethyl 2-methyl-4-n-propyl-3(ethylsulfanylcarbonyl)-6-phenylpyridine-5-carboxylate, 5-benzyl 2-methyl-4-ethyl-3-(ethylsulfanylcarbonyl)-6-phenylpyridine-5-carboxylate, 3-ethyl 5-benzyl-2-methyl-4-phenylethynyl-6-cyclobutylpyridine-3,5-dicarboxylate, and 3-ethyl 5-benzyl-2-methyl-4-phenylethynyl-6-cyclopentylpyridine-3,5-dicarboxylate, Certain other embodiments of preferred compounds of formula (I) include those wherein $R_2$ is selected from the group consisting of ethyl, propyl, butyl, cyclobutyl, and methoxyethyl; $R_3$ is selected from the group consisting of ethylsulfanyl, and propylsulfanyl; $R_4$ is selected from the group consisting of methyl, ethyl, and propyl; $R_5$ is selected from the group consisting of ethyl, propyl, and hydroxyethyl; and $R_6$ is selected from the group consisting of phenyl, chlorophenyl, and cyclopentyl. Thus, specific examples of such compounds include 3,5-diethyl 2-ethyl-4-methyl-(3-ethylsulfanylcarbonyl)-6-phenylpyridine-3,5-dicarboxylate, 5-ethyl 2,4-diethyl-3-(ethylsulfanylcarbonyl)-6-phenylpyridine-5-carboxylate, 5-propyl 2,4-diethyl-3-(ethylsulfanylcarbonyl)-6-phenylpyridine-5-carboxylate, 5-propyl 2-ethyl-4-propyl-3-(ethylsulfanylcarbonyl)-6-phenylpyridine-5-carboxylate, 5-hydroxylethyl 2,4-diethyl-3-(ethylsulfanylcarbonyl)-6-phenylpyridine-5-carboxylate, 5-ethyl 2,4-diethyl-3-(ethylsulfanylcarbonyl)-6-(m-chlorophenyl)pyridine-5-carboxylate, 5-ethyl 2,4diethyl-3(ethylsulfanylcarbonyl)-6-cyclopentylpyridine-5-carboxylate, 5-ethyl 2,4diethyl-3-(propylsulfanylcarbonyl)-7-phenylpyridine-5-carboxylate, 5-propyl 2,4diethyl-3-(propylsulfanylcarbonyl)-6-(m-chlorophenyl)pyridine-5-carboxylate, 5-ethyl 2-propyl-4-ethyl-3-(ethylsulfanylcarbonyl)-6-phenylpyridine-5-carboxylate, 5-ethyl 2-(2-methoxyethyl)-4-ethyl-3-(ethylsulfanylcarbonyl)-6-phenylpyridine-5-carboxylate, 5-ethyl 2-butyl-4-ethyl-3-(ethylsulfanylcarbonyl)-6-phenylpyridine-5-carboxylate, and 5-ethyl 2-cyclobutyl-4-ethyl-3-(ethylsulfanylcarbonyl)-6-phenylpyride-5-carboxylate.

The present invention further provides compounds of formula (II)

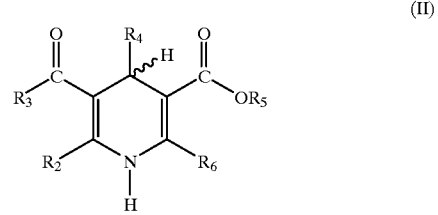

(II)

wherein $R_2$ is a $C_1$–$C_6$ alkyl; $R_3$ is selected from the group consisting of $C_1$–$C_6$ alkoxy, $C_1$–$C_6$ alkoxy $C_1$–$C_6$ alkylsulfanyl, and $C_1$–$C_6$ alkylsulfanyl; $R_4$ is selected from the group consisting of $C_1$–$C_6$ alkyl, acetal, formyl, aryl $C_2$–$C_6$ alkenyl, and aryl $C_2$–$C_6$ alkynyl; $R_5$ is selected from the group consisting of $C_1$–$C_6$ alkyl and aryl $C_1$–$C_6$ alkyl; and $R_6$ is selected from the group consisting of aryl and $C_3$–$C_6$ cycloalkyl; wherein said aryl is a phenyl or naphthyl. These compounds can be in the R or S form, or mixtures thereof.

Preferred embodiments of compounds of formula (II) include those wherein $R_2$ is a $C_1$–$C_6$ alkyl; $R_3$ is selected from the group consisting of $C_1$–$C_6$ alkoxy, $C_1$–$C_6$ alkoxy $C_1$–$C_6$ alkylsulfanyl, and $C_1$–$C_6$ alkylsulfanyl; $R_4$ is selected from the group consisting of $C_1$–$C_6$ alkyl, acetal, formyl, aryl $C_2$–$C_6$ alkenyl, and aryl $C_2$–$C_6$ alkynyl; $R_5$ is selected from the group consisting of $C_1$–$C_6$ alkyl and aryl $C_1$–$C_6$ alkyl; and $R_6$ is $C_3$–$C_6$ cycloalkyl. Examples of such compounds include 3-ethyl 5-benzyl 2-methyl-4-phenylethynyl-6-cyclopropyl-1,4-(±)-dihydropyridine-3,5-dicarboxylate, 3-ethyl 5-benzyl 2-methyl-4-phenylethynyl-6-cyclobutyl-1,4-(±)-dihydropyridine-3,5-dicarboxylate, 3-ethyl 5-benzyl 2-methyl-4-phenylethynyl-6-cyclopentyl-1,4-(±)-dihydropyridine-3,5-dicarboxylate, and 3-ethyl 5 benzyl 2-methyl-4 phenylethynyl-6-cyclohexyl-1,4-(±)-dihydropyridine-3,5-dicarboxylate.

Other preferred embodiments of the compounds of formula (II) include those wherein $R_2$ is a $C_1$–$C_6$ alkyl; $R_3$ is selected from the group consisting of $C_1$–$C_6$ alkoxy, $C_1$–$C_6$ alkoxy $C_1$–$C_6$ alkylsulfanyl, and $C_1$–$C_6$ alkylsulfanyl; $R_4$ is selected from the group consisting of $C_1$–$C_6$ alkyl, acetal, formyl, aryl $C_2$–$C_6$ alkenyl, and aryl $C_2$–$C_6$ alkynyl; $R_5$ is selected from the group consisting of $C_1$–$C_6$ alkyl and aryl $C_1$–$C_6$ alkyl; and $R_6$ is phenyl. Examples of such compounds include 3,5-diethyl 2, 4-dimethyl-6-phenyl-1,4-(±)-dihydropyridine-3,5-dicarboxylate, 3-propyl 5-ethyl-2,4-dimethyl-6-phenyl-1,4-(±)-dihydropyridine-3,5-dicarboxylate, 3,5-diethyl 2-methyl-4-ethyl-6-phenyl-1,4-(±)-dihydropyridine-3,5-dicarboxylate, 5-ethyl 2-methyl-4-ethyl-6-phenyl-3-(ethylsulfanylcarbonyl)-1,4-(±)-dihydropyridine carboxylate, 5-ethyl 2-methyl-4-ethyl-6-phenyl-3-(2-methoxyethylsulfanylcarbonyl)-1,4-(±)-dihydropyridine-5-carboxylate, 5-ethyl 2-methyl-4-propyl-6-phenyl-3-(ethylsulfanylcarbonyl)-1,4-(±)-dihydropyridine-5-carboxylate, 5-benzyl 2-methyl-4-ethyl-6-phenyl-3-(ethylsulfanylcarbonyl)-1,4-(±)-dihydropyridine-5-carboxylate, 3,5-diethyl 2-methyl-6-phenyl-4-(dimethoxymethyl)-1,4-(±)-dihydropyridine-3,5dicarboxylate, 3,5-diethyl 2-ethyl-6-phenyl-4-methyl-1,4-(±)-dihydropyridine-3,5-dicarboxylate, 5-ethyl 2,4-diethyl-6-phenyl-3-(ethylsulfanylcarbonyl)-1,4-(±)-dihydropyridine-5-carboxylate, and 5-ethyl 2-propyl-4-ethyl-6-phenyl-3-(ethylsulfanylcarbonyl)-1,4-(±)-dihydropyridine-5-carboxylate, or a pharmaceutically acceptable salt thereof.

The dihydropyridines of the present invention can be prepared by methods known to those skilled in the art For example, the Hantzsch condensation involving a 3-amino-2-propenoate ester, an aldehyde, and a β-ketoester. The corresponding pyridines can be prepared by the oxidation of the dihydropyridines using, for example, tetrachloroquinone as the oxidant.

The pyridine derivatives of the present invention are particularly advantageous because they are in an oxidized state compared to the corresponding dihydropyridine derivatives. The oxidation causes (i) the loss of the chiral center and consequently a change in the spatial position of the substituent in 4-position, (ii) the formation of a stable aromatic system; and (iii) a decrease of the pKa value. Some or all these factors can modify affinities and selectivities of the pyridine derivatives in comparison to the dihydropyridine derivatives.

All of the aforesaid compounds of the present invention can be used as is or in the form of a composition, e.g., a pharmaceutical composition, comprising a carrier, e.g., a pharmaceutically acceptable carrier, and an amount, e.g., a therapeutically effective amount, of any of the compounds of formulas (I) and (II).

The present invention further provides a method of treating a mammal comprising selectively blocking one or more of the adenosine receptors of the mammal, particularly the $A_3$ adenosine receptors, by administering to the mammal at least one compound of formulas (I) and (II).

The pharmaceutically acceptable carriers described herein for example, vehicles, adjuvants, excipients, or diluents, are well-known to those who are skilled in the art and are readily available to the public. It is preferred that the pharmaceutically acceptable carrier be one which is chemically inert to the active compound and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral aerosol, parenteral, subcutaneous, intravenous, intraarterial, intramuscular, interperitoneal, intrathecal, rectal and vaginal administration are merely exemplary and are in no way limiting.

Formulations suitable for oral administration can consist of (a) liquid solutions, such as an effective amount of the compound dissolved in diluents, such as water, saline, or. orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol benzyl alcohol, and the polyethylene alcohols and polyethylene glycols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxde, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, and synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactants in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238–250 (1982), and *ASHP Handbook on Injectable Drugs*, Toissel, 4th ed., pages 622–630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The compounds of the present invention can be used in the treatment of any disease state or condition involving the release of inositol-1,4,5-triphosphate (IP3), diacylglycerol (DAG), and free radicals and subsequent arachidonic acid cascades Thus, high blood pressure, locomotor hyperactivity, hypertension, acute hypoxia, depression, and infertility can be treated in accordance with the present inventive method, wherein one of the above-described compounds is acutely administered, e.g., within about a few minutes to about an hour of the onset or realization of symptoms. The method also has utility in the treatment of chronic disease states and conditions, in particular those conditions and disease states wherein chronic prophylactic or therapeutic administration of one of the above-described compounds will prevent the onset of symptoms or will reduce recovery time. Examples of disease states and conditions that may be treated in accordance with the present inventive method include inflammatory disorders, such as vascular inflammation and arthritis, allergies, Crohn's disease, asthma, wound healing, stroke, cardiac failure, acute spinal cord injury, acute head injury or trauma, seizure, neonatal hypoxia (cerebral palsy, prophylactic treatment involves chronic exposure through placental circulation), chronic hypoxia due to arteriovenous malformations and occlusive cerebral artery disease, severe neurological disorders related to excitotoxicity, Parkinson's disease, Huntington's chorea, and other diseases of the CNS, cardiac disease, kidney disease, and contraception.

These compounds can be significant cerebral protectants. K. A Jacobson, *Trends in Pharmacol. Sci.*, 19, 182–191 (May 1998). As such, the above compounds can be used to treat and/or protect against a variety of disorders, including, for example, seizures, transient ischemic shock, strokes, focal ischemia originating from thrombus or cerebral hemorrhage, global ischemia originating from cardiac arrest, trauma, neonatal palsy, hypovolemic shock, and hyperglycemia and associated neuropathies. The above method is applicable, for example, where a mammal has or is at risk of having a condition, disorder, or disease state associated with the cellular release of inositol-1,4,5-triphosphate or diacylglycerol. The method is also applicable when a mammal has or is at risk for hyperactivity and the compound in binding to the $A_3$ adenosine receptors functions as a locomotor depressant.

The present inventive method is also applicable when a mammal has or is at risk for hypertension and the compound in binding to the $A_3$ adenosine receptors functions as a hypotensive agent. The method is additionally applicable when a mammal has or is at risk for anxiety and the compound in binding to said $A_3$ adenosine receptors functions as an anxiolytic agent. The method is furthermore applicable when a mammal has or is at risk for cerebral ischemia and the compound in binding to the $A_3$ adenosine receptors functions as a cerebroprotectant. Moreover, the method is applicable when a mammal has or is at risk for seizures and the compound in binding to the $A_3$ adenosine receptors functions as an antiseizure agent.

The compounds of the present invention can be administered chronically as well as acutely.

The present inventive method includes the administration to an animal such as a mammal, particularly a human, in need of the desired adenosine receptor-dependent response of an effective amount, e.g., a therapeutically effective amount, of one or more of the aforementioned present inventive compounds or pharmaceutically acceptable salts or derivatives thereof alone or in combination with one or more other pharmaceutically active compounds.

The compounds of the present invention can also be administered as a pharmaceutically acceptable salt known to those skilled in the art. Example of suitable salts include carbonate, bicarbonate, sulfate, bisulfate, nitrate, halides, phosphates, oxalate, acetate, formate, citrates, and amino acid salts.

Some of the compounds of the present invention can be utilized as functionalized congeners for coupling to other molecules, such as amines and peptides. The use of such congeners provide for increased potency, prolonged duration of action, specificity of action, and prodrugs. Water solubility is also enhanced, which allows for reduction, if not complete elimination, of undesirable binding to plasma proteins and partition into lipids. Accordingly, improved pharmacokinetics can be realized.

The present invention further provides a method of characterizing an adenosine receptor, particularly an $A_3$ receptor, in a substrate comprising contacting the substrate with a compound of the present invention and evaluating the interaction of the compound and the adenosine receptor. The evaluation can provide qualitative information whether a binding has occurred as well as quantitative information as to the extent of binding.

The present invention further provides a method of inhibiting the binding of a ligand or test compound to an adenosine receptor, particularly an $A_3$ receptor, of a substrate comprising contacting the substrate with a compound of the present invention so that the compound of the present invention binds to the adenosine receptor and inhibits the ligand from binding to the adenosine receptor.

Thus, the compounds of the present invention can be used in vitro as adenosine receptor probes as well as in assays. Thus, for example, the compounds of the present invention may be used to isolate or characterize receptor sites in a cell or tissue. A labeled compound of the present invention can be used to assay the adenosine receptor binding ability of a ligand or test compound. The compounds of the present invention also can be used in vivo for studying their efficacy in the treatment of various diseases or conditions set forth earlier, e.g., those involving the release of IP3. The compounds of the present invention also can be used for angiogenesis.

One skilled in the art will appreciate that suitable methods of administering a compound of the present invention to an animal are available, and, although more than one route can be used to administer a particular compound, a particular route can provide a more immediate and more effective reaction than another route. Accordingly, the above-described methods are merely exemplary and are in no way limiting. The dose administered to an animal, particularly a human, in the context of the present invention should be sufficient to effect a prophylactic or other therapeutic response in the animal over a reasonable time frame. One skilled in the art will recognize that dosage will depend upon a variety of factors including the strength of the particular compound employed, the age, species, condition, and body weight of the animal as well as the severity/stage of the disease or condition. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states, in particular chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of selective adenosine receptor-dependent responses. Exemplary dosages range from about 0.01 to about 100 mg/kg body weight of the animal being treated/day. Preferred dosages range from about 0.1 to about 10 mg/kg body weight/day.

The abbreviations used in this application have the following meaning:

| | |
|---|---|
| [$^{125}$I]AB-MECA | [$^{125}$I]$N^6$-(4-amino-3-iodobenzyl)adenosine-5'-N-methyluronamide |
| CGS 21680 | 2-[4-[(2-carboxyethyl)phenyl]ethylamino]-5'-N-ethylcarbamoyladenosine |
| CHO | Chinese hamster ovary |
| HEK cells | Human embryonic kidney cells |
| DMF | N,N-dimethylformamide |
| DMSO | dimethylsulfoxide |
| $K_i$ | equilibrium inhibition constant |
| R-PIA | R-$N^6$-phenylisopropyladenosine |

The following examples further illustrate the present invention but, of course, should not be construed as in any way limiting its scope.

EXAMPLE 1

This Example illustrates the sources of some of the materials used in the synthesis of dihydropyrdine and pyridine derivatives of the present invention.

Ethyl 3-aminocrotonate (77c), aldehydes (78a–c and 78e), ethyl acetoacetate (79a), ethyl propionylacetate (79b), tetrachloro-1,4benzoquinone (80), acrolein dimethyl acetal (81), ethyl benzoylacetate, 2,2,6-trimethyl-4H-1,3-dioxin-4-one (84), benzyl acetate, N-isopropylcyclohexylamine, all acid chlorides (85, except 85f, obtained by the reaction of the precursor acid with thionyl chloride), 2,2-dimethyl-1,3-dioxane-4,6-dione (86), ethanethiol, propanethiol, and Dowex® 50X8-200 ion exchange resin were purchased from Aldrich (St. Louis, Mo.). 2-Methoxyethanethiol was prepared by a reported method. F. Tisato, et al., *J. Med. Chem.*, 39, 1258–1261 (1996). All other materials were obtained from commercial sources.

EXAMPLE 2

This Example illustrates the various analytical methods employed in the characterization of the compounds of the present invention.

Proton nuclear magnetic resonance spectroscopy was performed on a Varian GEMINI-300 spectrometer, and all spectra were obtained in CDCl$_3$. Chemical shifts (δ) reported herein are relative to tetramethylsilane. Chemical-ionization (CI) mass spectrometry was performed with a Finnigan 4600 mass spectrometer, and electron-impact (EI) mass spectrometry with a VG7070F mass spectrometer at 6 kV. Elemental analysis was performed by Atlantic Microlab Inc. (Norcross, Ga.). All melting points were determined with a Unimelt capillary melting point apparatus (Arthur H. Thomas Co., PA) and were uncorrected.

EXAMPLE 3

This Example illustrates the general procedure used for the preparation of certain 1,4-dihydropyridine compounds of the present invention. This Example also sets forth the $^1$H NMR and the high resolution mass spectral data. of these compounds.

Equimolar amounts (0.5–1.0 mmol) of the appropriate β-enaminoester (77), aldehyde (78), and β-ketoester (79) were dissolved in 2–5 mL of absolute ethanol. The mixture was sealed in a PYREX™ glass tube and heated, with stirring, to 80° C. for 18–24 h. After the mixture cooled to room temperature, the solvent was evaporated and the residue was purified by preparative TLC (silica 60; 1000 or 2000 mm; Analtech, Newark, DE; petroleum ether-ethyl acetate (4:1–9:1)). The products were shown to be homogeneous by analytical TLC and were stored at −20° C.

The $^1$H NMR and the high resolution mass spectral data of these compounds are set forth below:

3-Propyl 5-ethyl 2,4-dimethyl-6-phenyl-1,4-(±)-dihydropyridine-3,5-dicarboxylate (60)

$^1$NMR d: 0.91 (t, J=6.9 Hz, 3 H),1.00 (t, J=6.9 Hz, 3 H), 1.13 (d, J=6.9 Hz, 3 H), 1.72 (m, 2 H), 2.30 (s, 3 H), 3.88–4.00 (m, 3 H), 4.15 (m, 2 H), 5.69 (s, br, 1 H), 7.28–7.31 (m, 2 H), 7.39–7.42 (m, 3 H). MS (CI/NH$_3$): m/z 361 (M$^+$+NH$_4$), 344 (M$^+$+1). MS (EI): m/z 343 (M$^+$), 328 (M$^+$−CH$_3$, base), 314 (M$^+$−CH$_2$CH$_3$), 284 (M$^+$−OPr).

3,5-Diethyl 2-methyl-4-ethyl-6-phenyl-1,4-(±)-dihydropyridine-3,5-dicarboxylate (61)

$^1$H NMR d: 0.87–0.92 (m, 6 H), 1.31 (t, J=6.9 Hz, 3 H), 1.52 (m, 2 H), 2.32 (s, 3 H), 3.90 (m, 2 H), 4.03. (t, J=5.9 Hz, 1 H), 4.20 (m, 2 H), 5. 71 (s, br, 1 H), 7.30–7.40 (m, 5 H). MS (CI/NH$_3$): m/z 361 (M$^+$+NH$_4$, base), 344 (M$^+$+1), 3:14 (M$^+$−C$_2$H$_5$). MS (EI): m/z 314 (M$^{+-CH}{}_2$CH$_3$, base), 298 (M$^+$−OCH$_2$CH$_3$).

5-Ethel 2-methyl-4ethyl-6-phenyl-3-(ethylsulfanylcarbonyl)-1,4-(±)-dihydropyridine-5-carboxylate (62)

$^1$H NMR d: 0.90–0.96 (m, 6 H), 1.29 (t, J=7.8 Hz, 3 H), 1.57 (m, 2 H), 2.33 (s, 3 H), 2.93 (q, J=7.8 Hz, 2 H), 3.94 (q, J=6.9 Hz, 2 H), 4.03 (t, J=4.8 Hz, 1 H), 4.19 (q, J=6.0 Hz, 2 H), 5. 81 (s, br, 1 H), 7.30–7.32 (m, 2 H), 7.40–7.42 (m, 3 H). MS (CI/NH$_3$): m/z 377 (M$^+$+NH$_4$, base), 314 (M$^+$−OEt), 298 (M$^+$−SEt). MS (EI): m/z 330 (M$^+$−CH$_2$CH$_3$, base), 314 (M$^+$−OEt), 298 (M$^+$−SEt), 286 (M$^+$−CO$_2$Et).

5-Ethyl 2-methyl-4-ethyl-6-phenyl-3-[(2-methoxy-(ethylsulfanylcarbonyl)]-1,4-(±)-dihydropyridine-5-carboxylate (63)

$^1$H NMR d: 0.91 (t, J=7.8 Hz, 3H), 0.92 (t, J=7.8 Hz, 3 H), 1.60 (m, 2 H), 2.32 (s, 3 H), 3.14 (t, J=6.9 Hz, 2 H), 3.38 (s, 3 H), 3.55 (t, J=6.9 Hz, 2 H), 3.93 (q, J=7.8 Hz, 2 H), 4.20 (t, J=6.0 Hz, 1 H), 5.91 (s, br, 1 H), 7.28–7.32 (m, 2 H), 7.38–7.42 (m, 3 H). MS (CI/NH$_3$): m/z 405 (M$^+$+NH$_4$, base), 387 (M$^+$).

5-Ethyl 2-methyl-4-propyl-6-phenyl-3-(ethylsulfanylcarbonyl)-1,4-(±)-dihydropyridine-5-carboxylate (64)

$^1$NMR d: 0.90 (t, J=7.8 Hz, 3 H), 0.92 (t, J=7.8 Hz, 3 H), 1.29 (t, J=7.8 Hz, 3 H), 1.39 (m, 2 H), 1.49 (m, 2 H), 2.32 (s, 3 H), 2.92 (q, J=7.8 Hz, 2 H), 3.92 (q, J=7.8 Hz, 2 H), 4.19 (t, J=6.0Hz, 1 H), 5.98 (s, br, 1 H), 7.27–7.31 (m, 2 H), 7.38–7.41 (m, 3 H). MS (CI/NH$_3$): m/z 391 (M$^+$+NH$_4$, base), 373 (M$^+$). MS (EI): m/z 330 (M$^+$−CH$_2$CH$_2$CH$_3$, base), 314 (MH$^+$−OEt—Me), 284 (M$^+$−COSEt).

5-Benzyl 2-methyl-4ethyl-6-phenyl-3-(ethylsulfanylcarbonyl)-1,4-(±)-dihydropyridine-5-carboxylate (65)

$^1$H NMR d: 0.92 (t, J=7.8 Hz, 3 H), 1.29 (t, J=7.8 Hz, 3 H), 1.55–1.64 (m, 2 H), 2.32 (s, 3 H), 2.92 (q, J=7.8 Hz, 2 H), 4.24 (t, J=6.0 Hz, 1 H), 4.96 (AB, J=12.6 Hz, 2 H), 5.86 (s, br, 1 H), 6.98–7.00 (m, 1 H), 7.22–7.40 (m, 9 H). MS (CI/NH$_3$): m/z 439 (M$^+$+NH$_4$, base), 421 (M$^+$), 360 (M$^+$−SEt).

3,5-Diethyl 2-methyl-6-phenyl-4-(dimethoxymethyl)-1,4-(±)-dihydropyridine-3,5-dicarboxylate (66)

$^1$H NMR d:0.91(t, J=6.9 Hz, 3 H), 1.33 (t,J=6.9 Hz, 3 H), 2.33 (s, 3 H), 3.38 (s, 3 H), 3.39 (s, 3 H), 3.93 (q, J=6.9 Hz, 2 H), 4.14 (d, J=6.0 Hz, 1 H), 4.22 (q, J=6.9 Hz, 2 H), 4.48 (d, J=6.0 Hz, 2 H), 5.84 (s, br, 1 H), 7.31–7.35 (m, 2 H), 7.38–7.40 (m, 3 H). MS (CI/NH$_3$): m/z 407 (M$^+$+NH$_4$), 390 (M$^+$+1), 358 (M$^+$−OMe, base).

3-Ethyl 5-benzyl 2-methyl-4-phenylethynyl-6-cyclopropyl-1,4-(±)-dihydropyridine-3,5-dicarboxylate (70)

$^1$H NMR: δ0.59 (m, 1 H), 0.88–1.03 (m, 2 H), 1.18–1.28 (m, 1 H), 1.32 (t, J=7.8 Hz, 3 H), 2.31 (s, 3 H), 2.73–2.83 (m, 1 H), 4.17–4.35 (m, 2 H), 5.09 (s, 1 H), 5.29 (AB, J=12.9 Hz, 2H), 5.56 (s, br, 1 H), 7.22–7.47 (m, 10 H). MS (EI): m/z 441 ), 412 (M$^+$−CH$_2$CH$_3$,), 368 (M$^+$−CO$_2$Et), 350 (M$^+$−CH$_2$Ph), 306 (M$^+$−CO$_2$CH$_2$Ph), 91 (CH$_2$Ph, base).

3-Ethyl 5-benzyl 2-methyl-4-phenylethynyl-6-cyclobutyl-1,4-(±)-dihydropyridine-3,5-dicarboxylate (71)

$^1$H NMR: δ1.32 (t, J=6.9 Hz, 3 H), 1.79–2.29 (m, 6 H), 2.37–2.40 (m, 1 H), 2.38 (s, 3 H), 4.21–4.27 (m, 2 H), 5.07 (s, 1 H), 5.26 (AB, J=12.6 Hz, 2 H), 6.10 (s, br, 1 H), 7.21–7.46 (m, 10 H). MS (EI): m/z 455 (M$^+$), 426 (M$^+$−CH$_2$CH$_3$,), 382 (M$^+$−CO$_2$Et), 364 (M$^+$−CH$_2$Ph), 320 (M$^+$−CO$_2$CH$_2$Ph), 91 ($^+$CH$_2$Ph, base).

3-Ethyl 5-benzyl 2-methyl-4-phenylethynyl-6-cyclopentyl-1,4-(±)-dihydropyridine-3,5-dicarboxylate (72)

$^1$H NMR: δ1.23–1.37 (m, 4 H), 1.32 (t, J=6.9 Hz, 3 H), 1.70 (m, 4 H), 2.00 (m, 1 H), 2.35 (s, 3 H), 4.24 (m, 2 H), 5.09 (s, 1 H), 5.27 (AB, J=12.9 Hz, 2 H), 5.90 (s, br, 1 H), 7.22–7.46 (m, 10 H). MS (EI): m/z 487 (M$^+$+NH$_4$), 470 (M$^+$+1).

3-Ethyl 5-benzyl 2-methyl-4-phenylethynyl-6-cyclohexyl-1,4-(±)-dihydropyridine-3,5-dicarboxylate (73)

$^1$H NMR: δ1.13–1.38 (m, 6 H), 1.32 (t, J=6.9 Hz, 3 H), 1.65–1.89 (m, 5 H),2.35 (s, 3 H), 4.22 (q, J=6.9 Hz, 2 H), 5.09 (s, 1 H), 5.27 (AB, J=12.6 Hz, 2 H), 5.99 (s, br, 1 H), 7.21–7.46 (m, 10 H). MS (EI): m/z 483 (M$^+$), 454 (M$^+$−CH$_2$CH$_3$,), 400 (M$^+$−C$_6$H$_{11}$), 410 (M$^+$−CO$_2$Et), 392 (M$^+$−CH$_2$Ph), 348 (M$^+$−CO$_2$CH$_2$Ph), 91 ($^+$CH$_2$Ph, base).

3,5-Diethyl 2-ethyl-6-phenyl-4-methyl-1,4-(±)-dihydropyridine-3,5-dicarboxylate (74)

$^1$H NMR d: 0.90 (t, J=6.9 Hz, 3 H), 1.12 (d, J=6.9 Hz, 3 H), 1.19 (t, J=6.9 Hz, 3 H), 1.32 (t, J=6.9 Hz, 3 H), 2.50 (m, 1 H), 2.90 (m, 1 H), 3.89–3.98 (m, 3 H), 4.22 (m, 2 H), 5.73 (s, br, 1 H), 7.30–7.31 (m, 2 H), 7.40–7.42 (m, 3 H). MS (CI/NH$_3$): m/z 361 (M$^+$+NH$_4$), 344 (M$^+$+1). MS (EI): m/z 343 (M$^+$), 328 (M$^+$−CH$_3,$ base), 298 (M$^+$−OEt).

5-Ethyl 2,4-diethyl-6-phenyl-3-(ethylsulfanylcarbonyl)-1,4-(±)-dihydropyridine-5-carboxylate (75)

$^1$H NMR d: 0.89 (m, 6 H), 0.93 (t, J=6.9 Hz, 3 H), 1.19 (t, J=7.8 Hz, 3 H), 1.58 (m, 2 H), 2.69 (m, 2 H), 2.92 (q,

J=7.8 Hz, 2 H), 3.92 (q, J=6.9 Hz, 2 H , 4.02 (t, J=6.0 Hz, 1 H), 5.94 (s, br, 1 H), 7.32 (m, 2 H), 7.41 (m, 3 H). MS (CI/NH$_3$): m/z 391 (M$^+$+NH$_4$ base), 374 (M$^+$+1), 312 (M$^+$-SEt). MS (EI): m/z 373 (M$^+$), 344 (M$^+$-CH$_2$CH$_3$), 328 (M$^+$-OEt, base), 312 (M$^+$-SEt).

5-Ethyl 2-propyl-4-ethyl-6-phenyl-3-(ethylsulfanylcarbonyl)-1,4-(±)-dihydropyridine-5-carboxylate (76)

$^1$H NMR d: 0.90–0.96 (m, 6 H), 0.99 (t, J=7.8 Hz, 3 H), 1.29 (t J=7.8 Hz, 3 H), 1.53–1.66 (m, 4 H), 2.66 (m, 2 H), 2.92 (q, J=6.9 H 2 H), 3.95 (q, J=7.8 Hz, 2 H), 4.20 (t, J=6.0 Hz, 1 H), 5.85 (s, br, 1 H), 7.30–7.32 (m, 2 H), 7.41–7.43 (m, 3 H). MS (CI/NH$_3$): m/z 405 (MS$^+$+NH$_4$), 388 (M$^+$+1), 326 (M$^+$-SEt).

EXAMPLE 4

Figure 3:
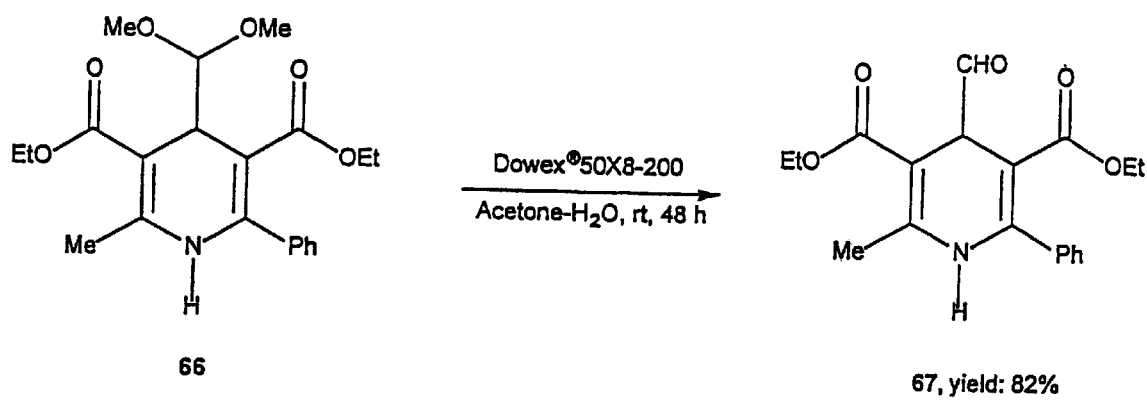
FIG. 3 depicts a method of synthesis of a dihydropyridine derivative containing an aldehyde group (67) from a dihydropyridine derivative containing an acetal (66).

This Example illustrates a preparation of an aldehyde group containing dihydropyridine. The reaction involved is illustrated in FIG. 3.

Dihydropyridine 66 (14 mg) and a catalytic amount of Dowex® 50X8-200 resin were stirred in a mixture of acetone (2 mL) and water (0.5 mL) at room temperature for 48 h. The resin was filtered off, and the filtrate was dried with anhydrous MgSO$_4$. The solvent was removed, and the residue was purified with preparative TLC (silica 60; 1000 mm; Analtech, Newark, DE; petroleum ether-ethyl acetate (3:1)) to give 10 mg of the desired product.

3,5-Diethyl 2-methyl-6-phenyl-4-formyl-1,4(±)-dihydropyridine-3,5-dicarboxylate (67), yield: 82%. The $^1$HNMR and high resolution mass spectral data of 67 are set forth below.

$^1$H NMR d: 0.89 (t, J=6.9 Hz, 3 H), 1.32 (t, J=6.9 Hz, 3 H), 2.37 (s, 3 H), 3.94 (q, J=6.9 Hz, 2 H), 4.24 (d, J=6.9 Hz, 2 H), 4.90 (s, 1 H), 5.81 (s, br, 1 H), 7.35 (m, 2 H), 7.41 (m, 3 H), 9.66 (s, 1 H). MS (CI/NH$_3$): m/z 361 (M$^+$+NH$_4$), 344 (M$^+$+1), 314 (M$^+$-CHO, base). MS (EI): m/z 343 (M$^+$-), 314 (M$^+$-CHO, base), 298 (M$^+$-OEt). HRMS: Calcd. for C$_{18}$H$_{20}$NO$_4$ (M$^+$-CHO) 314.1392; found, 314.1432.

EXAMPLE 5

Figure 4:
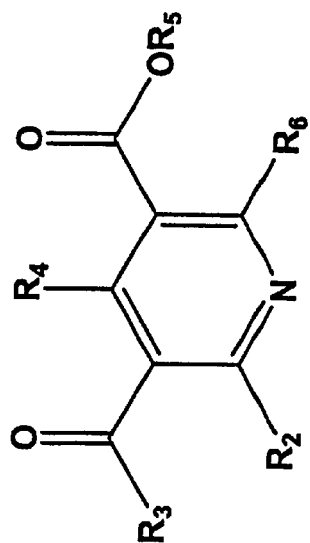
FIG. 4 depicts a method of synthesis of pyridine derivatives 34–41, 44, 46–48, and 55, starting from dihydropyridine derivatives 60–67, 71, 72, and 74–76.
Figure 4:
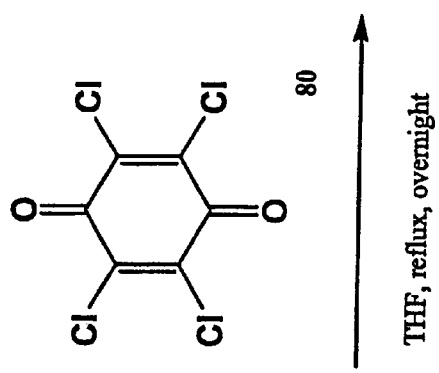
Figure 4:
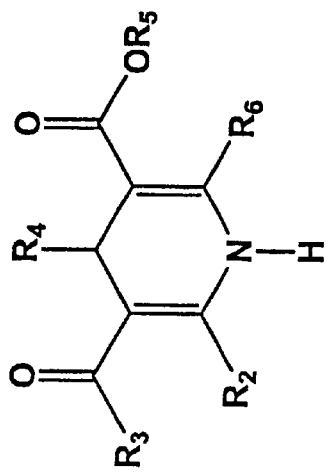
Figure 5:
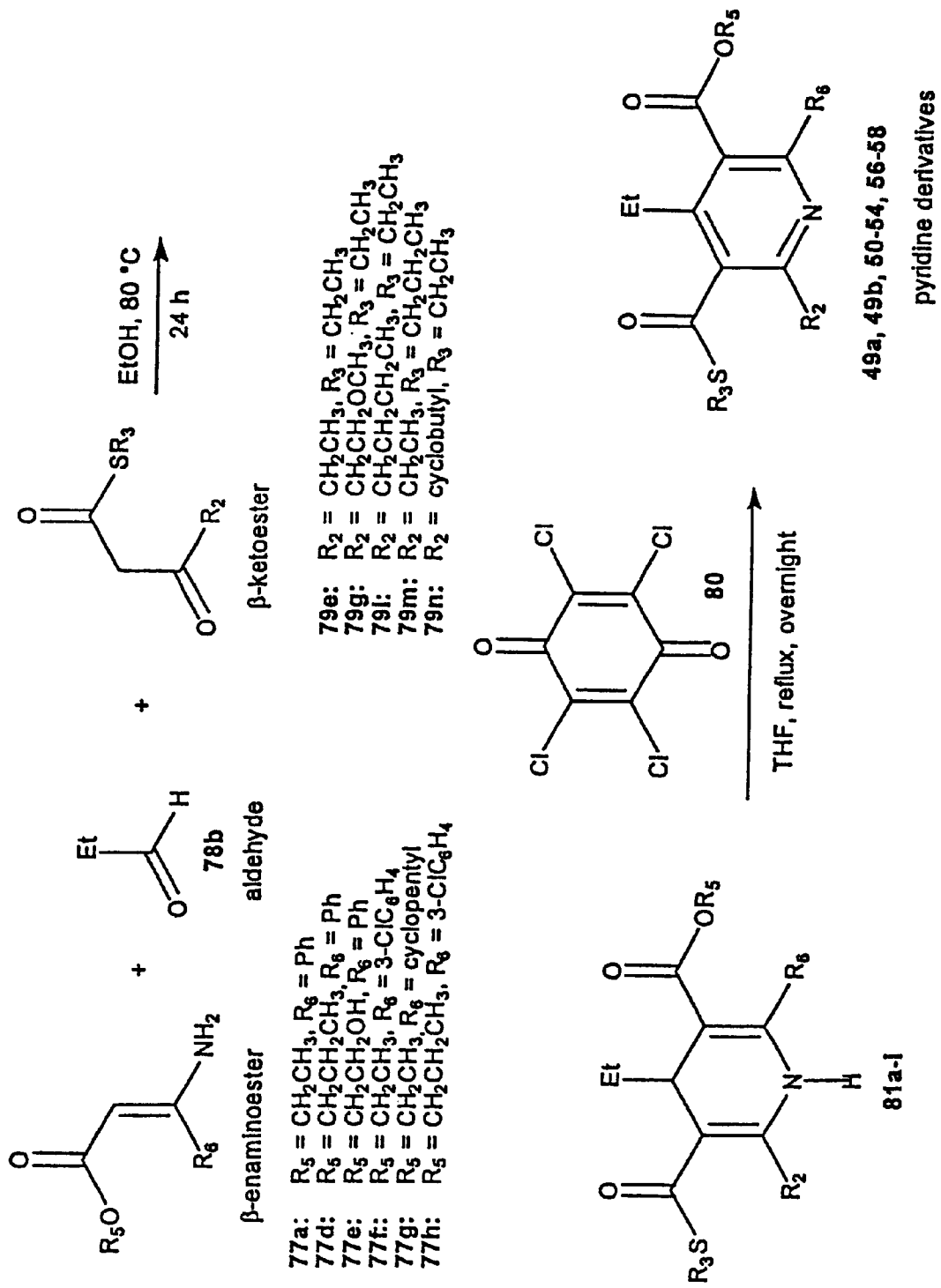
FIG. 5 depicts a method of synthesis of pyridine derivatives 49a, 49b, 50–54, and 56–58, starting from a β-enaminoester (77a, and 77d–h), an aldehyde (78b), and a β-ketoester (79e, 79g, and 79l–n)

This Example illustrates a procedure for the oxidation of the 1,4-dihydropyridines into the corresponding pyridine derivatives. The reaction is schematically shown in FIG. 4.

Equimolar amounts of the 1,4-dihydropyrdines (60–67, 70–76, 81a–i, ~0.2 mmol) and tetrachloro-1,4-benzoquinone (80) in THF (2–4 mL) were mixed and refluxed overnight. After the mixture cooled to room temperature, the solvent was removed, and the residue was purified by preparative TLC (silica 60; 1000 mm; Analtech, Newark, Del.; petroleum ether-ethyl acetate (9:1-19:1)) to give the desired products. The $^1$H NMR and high resolution mass spectral data of some of the pyridine compounds of the present invention are set forth below.

3-Propyl 5-ethyl 2,4-dimethyl-6-phenylpyridine-3,5-dicarboxylate (34)

$^1$H NMR d: 0.97–1.06 (m, 6 H), 1.81 (m, 2 H), 2.37 (s, 3 H), 2.61 (s, 3 H), 4.11 (t, J=6.9 Hz, 2 H), 4.35 (t, J=6.9 Hz, 2 H), 7.40–7.43 (m, 3 H), 7.56–7.57 (m, 2 H). MS (EI): m/z 341 (M$^+$), 312 (M$^+$-CH$_2$CH$_3$, base), 296 (M$^+$-OCH$_2$CH$_3$), 282 (M$^+$-OPr). HRMS: calcd for C$_{20}$H$_{23}$NO$_4$ 341.1627, found 341.1635.

3,5-Diethyl 2-methyl-4-ethyl-6-phenylpyridine-3,5-dicarboxylate (35)

$^1$H NMR d: 0.97 (t, J=6.9 Hz, 3 H), 1.24 (t, J=7.8 Hz, 2 H), 1.43 (t, J=6.9 Hz, 3 H), 2.61 (s, 3 H), 2.71 (q, J=7.8 Hz, 2 H), 4.09 (q, J=6.9 Hz, 2 H), 4.46 (q, J=6.9 Hz, 2 H), 7.40–7.43 (m,3 H), 7.55–7.58 (m, 2 H). MS (EI): m/z 341 (M$^+$), 312 (M$^+$-CH$_2$CH$_3$, base), 296 (M$^+$-OCH$_2$CH$_3$), 284 (MH$^+$-2xEt), 268 (M$^+$-CO$_2$Et), 240 (MH$^+$-Et—CO$_2$Et). HRMS: calcd. for C$_{20}$H$_{23}$NO$_4$ 341.1627, found 341.1615.

5-Ethyl 2-methyl-4-ethyl-3-(ethylsulfanylcarbonyl)-6-phenylpyridine-5-carboxylate (36)

$^1$H NMR d: 0.97 (t, J=6.9 Hz, 3 H), 1.23 (t, J=7.8 Hz, 3 H), 1.41 (t, J=7.8 Hz, 3 H), 2.61 (s, 3 H), 2.74 (q, J=7.8 Hz, 2 H), 3.14 (q, J=7.8 Hz, 2 H), 4.09 (q, J=6.9 Hz, 2 H), 7.40–7.44 (m, 3 H), 7.56–7.59 (m, 2 H). MS (CI/NH$_3$): m/z 375 (M$^+$+NH$_4$), 358 (M$^+$+1, base). MS (EI): m/z 357 (M$^+$), 312 (M$^+$-OEt), 296 (M$^+$-SEt, base), 268 (M$^+$-COSEt).

5-Ethyl 2-methyl-4-ethyl-3-[2-methoxy-(ethylsulfanylcarbonyl)]-6-phenylpyridine-5-carboxylate (37)

$^1$H NMR d: 0.97 (t, J=7.8 Hz, 3 H), 1.23 (t, J=7.8 Hz, 3 H), 2.62 (s, 3 H), 2.74 (q, J=7.8 Hz, 2 H), 3.36 (t, J=6.0 Hz, 2 H), 3.42 (s, 3 H), 3.67 (t, J=6.0 Hz, 2 H), 4.09 (q, J=7.8 Hz, 2 H), 7.39–7.42 (m, 3 H), 7.55–7.58 (m, 2 H). MS (CI/NH$_3$): m/z 388 (M$^+$+1), 296 (M$^+$-CH$_3$OCH$_2$CH$_2$S).

5-Ethyl-2-methyl-4-propyl-3-(ethylsulfanylcarbonyl)-6-phenylpyridine-5-carboxylate (38)

$^1$H NMR d: 0.95 (t, J=6.9 Hz, 3 H), 0.97 (t, J=6.9 Hz, 3 H), 1.41 (t, J=7.8 Hz, 3 H), 1.63 (m, 2 H), 2.61 (s, 3 H), 2.68 (t, J=7.8 Hz, 2 H), 3.14 (q, J=6.9 Hz, 2 H), 4.08 (q, J=6.9 Hz, 2 H), 7.41 (m, 3 H), 7.56 (m, 2 H). MS (CI/NH$_3$): m/z 372 (M$^+$+1). MS (EI): m/z 326 (M$^+$-OCH$_2$CH$_3$), 310 (M$^+$-SEt, base), 282 (M$^+$-COSEt).

5-Benzyl 2-methyl-4-ethyl-3-(ethylsulfanylcarbonyl)-6-phenylpyridine-5-carboxylate (39)

$^1$H NMR d: 1.18 (t, J=7.8 Hz, 3 H), 1.40 (t, J=7.8 Hz, 3 H), 2.60 (s, 3 H), 2.70 (q, J=7.8 Hz, 2 H), 3.12 (q, J=7.8 Hz, 2 H), 5.04 (s, 2 H), 6.96–6.98 (m, 2 H), 7.22–7.28 (m, 3 H), 7.38–7.40 (m, 3 H), 7.55–7.58 (m, 2 H). MS (CI/NH$_3$): m/z 420 (M$^+$1, base).

3,5-Diethyl 2-methyl-4-(dimethoxymethyl)-6-phenylpyridine-3,5-dicarboxylate (40)

$^1$H NMR d: 1.00 (t, J=6.9 Hz, 3 H), 1.41 (t, J=6.9 Hz, 3 H), 2.62 (s, 3 H), 3.33 (s, 6 H), 4.07 (q, J=6.9 Hz, 2 H), 4.41 (d, J=6.9 Hz, 2 H), 5.76 (s, 1 H), 7.40–7.42 (m, 3 H), 7.53–7.55 (m, 2 H). MS (CI/NH$_3$): m/z 388 (M$^+$+1). HRMS: calcd for C$_{21}$H$_{25}$NO$_6$ 387.1682, found 387.1674.

3,5-Diethyl 2-methyl-4-formyl-6-phenylpyridine-3,5-dicarboxylate (41)

$^1$H NMR d: 1.06 (t, J=7.8 Hz, 3 H), 1.43 (t, J=6.9 Hz, 3 H), 2.94 (s, 3 H), 4.17 (q, J=7.8 Hz, 2 H), 4.42 (d, J=6.9 Hz, 2 H), 7.43–7.45 (m, 3 H), 7.55 (m, 2 H), 8.63 (s, 1 H). MS (CI/NH$_3$): m/z 342 (M$^+$+1).

3-Ethyl 5-benzyl 2-methyl-4-phenylethynyl-6-cyclobutylpyridine-3,5-dicarboxylate (44)

$^1$H NMR: δ1.37 (t, J=7.8 Hz, 3 H), 1.81–1.98 (m, 2 H), 2.11–2.19 (m, 2 H), 2.37–2.47 (m, 2 H), 2.61 (s, 3 H), 3.70 (m, 1 H), 4.43 (q, J=7.8 Hz, 2 H), 5.39 (s, 2 H), 7.28–7.40 (m, 10 H). MS (EI): m/z 454 (M$^+$+1).

3-Ethyl 5-benzyl 2-methyl-4-phenylethynyl-6-cyclopentylpyridine-3,5-dicarboxylate (45)

$^1$H NMR: δ1.37 (t, J=7.8 Hz, 3 H), 1.54–1.58 (m, 2 H), 1.78–1.88 (m, 6 H) 2.57 (s, 3 H), 3.04 (m, 1 H), 4.43 (q, J=7.8 Hz, 2 H), 5.41 (s, 2 H), 7.29–7.44 (m, 10 H). MS (EI): m/z 467 (M$^+$), 376 (M$^+$–CH$_2$Ph), 91 ($^+$CH$_2$Ph, base).

3,5-Diethyl 2-ethyl-4-methyl-6-phenylpyridine-3,5-dicarboxylate (46)

$^1$H NMR d: 1.00 (t, J=6.9 Hz, 3 H), 1.33 (t, J=7.8 Hz, 3 H), 1.42 (t, J=6.9 Hz, 3 H), 2.36 (s, 3 H), 2.86 (q, J=7.8 Hz, 2 H), 4.12 (q, J=6.9 Hz, 2 H), 4.45 (q, J=6.9 Hz, 2 H), 7.40–7.43 (m, 3 H), 7.58–7.60 (m, 2 H). MS (EI): m/z 341 (M$^+$), 312 (M$^+$–CH$_2$CH$_3$, base), 296 (M$^+$–OEt), 284 (MH$^+$–2xEt), 269 (MH$^+$–CO$_2$Et). HRMS: calcd for C$_{20}$H$_{23}$NO$_4$ 341.1627, found 341.1631.

2-Methyl-4-ethyl-5-ethoxycarbonyl-6-phenylpyridine-3-carboxylic acid (47)

$^1$H NMR d: 0.97 (t, J=7.8 Hz, 3 H), 1.24 (t, J=7.8 Hz, 3 H), 2.61 (s, 3 H), 2.71 (q, J=7.8 Hz, 2 H), 4.46 (J=7.8 Hz, 2 H), 7.40–7.45 (m, 3 H), 7.55–7.59 (m, 2 H). MS (CI/NH$_3$): m/z 314 (M$^+$1). MS (EI): m/z 312 (M$^+$–1), 296 (M$^+$–OH), 284 (M$^+$–Et, base).

5-Ethyl 2,4-diethyl-3-(ethylsulfanylcarbonyl)-6-phenylpyridine-5-carboxylate (48)

$^1$H NMR d: 0.98 (t, J=7.8 Hz, 3 H), 1.23 (t, J=7.8 Hz, 3 H), 1.34 (t, J=6.9 Hz, 3 H), 1.41 (t, J=7.8 Hz, 3 H), 2.73 (q, J=7.8 Hz, 2 H), 2.87 (q, J=7.8 Hz, 2 H), 3.14 (q, J=7.8 Hz, 2 H), 4.10 (q, J=6.9 Hz, 2 H), 7.41–7.44 (m, 3 H), 7.58–7.61 (m, 2 H). MS (CI/NH$_3$): m/z 372 (M$^+$+1, base).

5-Propyl 2,4-diethyl-3-(ethylsulfanylcarbonyl)-6-phenylpyridine-5-carboxylate (49a)

$^1$H NMR d: 0.65 (t, J=7.8 Hz, 3 H), 1.23 (t, J=7.8 Hz, 3 H), 1.34 (t, J=7.8 Hz, 3 H), 1.41 (t, J=7.8 Hz, 3 H), 1.34–1.44 (m, 2 H), 2.73 (q, J=7.8 Hz, 2 H), 2.87 (q, J=7.8 Hz, 2 H), 3.14 (q, J=7.8 Hz, 2 H), 3.99 (t, J=6.9 Hz, 2 H), 7.40–7.44 (m, 3 H), 7.59–7.62 (m, 2 H). MS (CI/NH$_3$): m/z 404 (MH$^+$+NH$_4$), 386 (M$^+$+1, base).

5-Propyl 2-ethyl-4-propyl-3-(ethylsulfanylcarbonyl)-6-phenylpyridine-5-carboxylate (49b)

$^1$H NMR d: 0.66 (t, J=7.8 Hz, 3 H), 0.95 (t, J=7.8 Hz, 3 H), 1.34 (t, J=7.8 Hz, 3 H), 1.41 (t, J=7.8 Hz, 3 H), 1.40 (m, 2 H), 1.63 (m, 2 H), 2.66 (t, J=7.8 Hz, 2 H), 2.86 (q, J=7.8 Hz, 2 H), 3.13 (q, J=7.8 Hz, 2 H), 3.98 (t, J=6.9 Hz, 2 H), 7.39–7.44 (m, 3 H), 7.58–7.62 (m, 2 H). MS (CI/NH$_3$): m/z 400 (M$^+$+1, base).

5-Hydroxylethyl 2,4-diethyl-3-(ethylsulfanylcarbonyl)-6-phenylpyridine-5-carboxylate (40)

$^1$H NMR d: 1.24 (t, J=7.8 Hz, 3 H), 1.34 (t, J=7.8 Hz, 3 H), 1.42 (t, J=7.8 Hz, 3 H), 2.75 (q, J=7.8 Hz, 2 H), 2.87 (q, J=7.8 Hz, 2 H), 3.15 (q, J=7.8 Hz, 2 H), 3.48 (m, 2 H), 4.13 (t, J=4.8 Hz, 2 H), 7.45–7.49 (m, 3 H), 7.60–7.63 (m, 2 H). MS (CI/NH$_3$): m/z 404 (M$^+$+NH$_4$–1), 388 (M$^+$+1).

5-Ethyl 2,4-diethyl-3-(ethylsulfanylcarbonyl)-6-(m-chlorophenyl)pyridine-5-carboxylate (51)

$^1$H NMR d: 1.07 (t, J=7.8 Hz, 3 H), 1.23 (t, J=7.8 Hz, 3 H), 1.34 (t, J=7.8 Hz, 3 H), 1.41 (t, J=7.8 Hz, 3 H), 2.72 (q, J=7.8 Hz, 2 H), 2.86 (q, J=7.8 Hz, 2 H), 3.14 (q, J=7.8 Hz, 2 H), 4.16 (q, J=7.8 Hz, 2 H), 7.35–7.41 (m, 1 H), 7.46–7.50 (m, 1 H), 7.62 (s, 1 H). MS (CI/NH$_3$): m/z 406 (M$^+$+1).

5-Ethyl 2,4-diethyl-3-(ethylsulfanylcarbonyl)-6-cyclopentylpyridine-5-carboxylate (52)

$^1$H NMR d: 1.18 (t, J=7.8 Hz, 3 H), 1.27 (t, J=7.8 Hz, 3 H), 1.38 (t, J=7.8 Hz, 3 H), 1.39 (t, J=7.8 Hz, 3 H), 1.63 (m, 2 H), 1.92 (m, 7 H), 2.58 (q, J=7.8 Hz, 2 H), 2.76 (q, J=7.8 Hz, 2 H), 3.91 (q, J=7.8 Hz, 2 H), 4.40(q, J=7.8 Hz, 2 H). HRMS: calcd for C$_{20}$H$_{29}$NO$_3$S 363.1868, found 363.1858.

5-Ethyl 2,4-diethyl-3-propylsulfanylcarbonyl-6-phenylpyridine-5-carboxylate (53)

$^1$H NMR d: 0.98 (t, J=7.8 Hz, 3 H), 1.07 (t, J=7.8 Hz, 3 H), 1.23 (t, J=7.8 Hz, 3 H), 1.34 (t, J=7.8 Hz, 3 H), 1.76 (m, 2 H), 2.73 (q, J=7.8 Hz, 2 H), 2.87 (q, J=7.8 Hz, 2 H), 3.12 (q, J=7.8 Hz, 2 H), 4.10 (q, J=7.8 Hz, 2 H), 7.42–7.43 (m, 3 H), 7.58–7.61 (m, 2 H). MS (CI/N$_3$): m/z 386 (M$^+$+1, base).

5-Propyl 2,4-diethyl-3-propylsulfanylcarbonyl-6-(m-chlorophenyl)pyridine-5-carboxylate (54)

$^1$H NMR d: 0.72 (t, J=7.8 Hz, 3 H), 1.07 (t, J=7.8 Hz, 3 H), 1.23 (t, J=7.8 Hz, 3 H), 1.34 (t, J=7.8 Hz, 3 H), 1.46 (m, 2 H), 1.77 (m, 2 H), 2.72 (q, J=7.8 Hz, 2 H), 2.86 (q, J=7.8 Hz, 2 H), 3.13 (t, J=6.9 Hz, 2 H), 4.04 (t, J=6.9 Hz, 2 H), 7.37 (m, 2 H), 7.48 (m, 1 H), 7.62 (s, 1 H). MS (CI/NH$_3$): m/z 434 (M$^+$(C$_{23}$H$_{28}$$^{35}$ClNO$_3$S)+1, base), 404 (M$^+$–C$_2$H$_5$), 358 (M$^+$–PrS).

5-Ethyl 2-propyl-4-ethyl-3-(ethylsulfanylcarbonyl)-6-phenylpyridine-5-carboxylate (55)

$^1$H NMR d: 0.99 (t, J=6.9 Hz, 6 H), 1.23 (t, J=7.8 Hz, 3 H), 1.41 (t, J=7.8 Hz, 3 H), 1.82 (m, 2 H), 2.72 (q, J=6.9 Hz, 2 H), 2.81 (q, J=6.9 Hz, 2 H), 3.14 (q, J=7.8 Hz, 2 H), 4.10 (q, J=7.8 Hz, 2 H), 7.40–7.44 (m, 3 H), 7.57–7.60 (m, 2 H). MS (EI): m/z 385 (M$^+$), 340 (M$^+$–OEt), 324 (M$^+$–SEt), 296 (M$^+$–COSEt).

5-Ethyl 2-(2-methoxylethyl)-4-ethyl-3-(ethylsulfanylcarbonyl)-6-phenylpyridine-5-carboxylate (56)

$^1$H NMR d: 0.99 (t, J=7.8 Hz, 3 H), 1.23 (t, J=7.8 Hz, 3 H), 1.41 (t, J=7.8 Hz, 3 H), 2.73 (q, J=7.8 Hz, 2 H), 3.11–3.18 (m, 4 H), 3.37 (s, 3 H), 3.85 (t, J=7.8 Hz, 2 H), 4.10 (q, J=7.8 Hz, 2 H), 7.42–7.44 (m, 3 H), 7.58–7.61 (m, 2 H). MS (CI/NH$_3$): m/z 402 (MH$^+$, base). HRMS: calcd. for C$_{22}$H$_{27}$NO$_4$S 401.1661, found 401.1666.

5-Ethyl 2-butyl-4-ethyl-3-(ethylsulfanylcarbonyl)-6-phenylpyridine-5-carboxylate (49a)

$^1$H NMR d: 0.65 (t, J=7.8 Hz, 3 H), 1.23 (t, J=7.8 Hz, 3 H), 1.34 (t, J=7.8 Hz, 3 H), 1.41 (t, J=7.8 Hz, 3 H), 1.34–1.44 (m, 2 H), 2.73 (q, J=7.8 Hz, 2 H), 2.87 (q, J=7.8 Hz, 2 H), 3.14 (q, J=7.8 Hz, 2 H), 3.99 (t, J=6.9 Hz, 2 H), 7.40–7.44 (m, 3 H), 7.59–7.62 (m, 2 H). MS (CI/NH$_3$): m/z 404 (MH$^+$+NH$_4$), 386 (M$^+$+1, base).

5-Propyl 2-ethyl-4-propyl-3-(ethylsulfanylcarbonyl)-6-phenylpyridine-5-carboxylate (49b)

$^1$H NMR d: 0.66 (t, J=7.8 Hz, 3 H), 0.95 (t, J=7.8 Hz, 3 ), 1.34 (t, J=7.8 Hz, 3 H), 1.41 (t, J=7.8 Hz, 3 H), 1.40 (m, 2 H), 1.63 (m, 2 H), 2.66 (t, J=7.8 Hz, 2 H), 2.86 (q, J=7.8

Hz, 2 H), 3.13 (q, J=7.8 Hz, 2 H), 3.98 (t, J=6.9 Hz, 2 H), 7.39–7.44 (m, 3 H), 7.58–7.62 (m, 2 H). MS (CI/NH$_3$): m/z 400 (M$^+$+1, base).

5-Hydroxylethyl 2,4-diethyl-3-(ethylsulfanylcarbonyl)-6-phenylpyridine-5-carboxylate (40)

$^1$H NMR d: 1.24 (t, J=7.8 Hz, 3 H), 1.34 (t, J=7.8 Hz, 3 H), 1.42 (t, J=7.8 Hz, 3 H), 2.75 (q, J=7.8 Hz, 2 H), 2.87 (q, J=7.8 Hz, 2 H), 3.15 (q, J=7.8 Hz, 2 H), 3.48 (m, 2 H), 4.13 (t, J=4.8 Hz, 2 H), 7.45–7.49 (m, 3 H), 7.60–7.63 (m, 2 H). MS (CI/NH$_3$): m/z 404 (M$^+$+NH$_4$–1), 388 (M$^+$1).

5-Ethyl 2,4-diethyl-3-(ethylsulfanylcarbonyl)-6-(m-chlorophenyl)pyridine-5-carboxylate (51)

$^1$H NMR d: 1.07 (t, J=7.8 Hz, 3 H), 1.23 (t, J=7.8 Hz, 3 H), 1.34 (t, J=7.8 Hz, 3 H), 1.41 (t, J=7.8 Hz, 3 H), 2.72 (q, J=7.8 Hz, 2 H), 2.86 (q, J=7.8 Hz, 2 H), 3.14 (q, J=7.8 Hz, 2 H), 4.16 (q, J=7.8 Hz, 2 H), 7.35–7.41 (m, 1 H), 7.46–7.50 (m, 1 H), 7.62 (s, 1 H). MS (CI/NH$_3$): m/z 406 (M$^+$+1).

5-Ethyl 2,4-diethyl-3-(ethylsulfanylcarbonyl)-6-cyclopentylpyridine-5-carboxylate (52)

$^1$H NMR d: 1.18 (t, J=7.8 Hz, 3 H), 1.27 (t, J=7.8 Hz, 3 H), 1.38 (t, J=7.8 Hz, 3 H), 1.39 (t, J=7.8 Hz, 3 H), 1.63 (m, 2 H), 1.92 (m, 7 H), 2.58 (q, J=7.8 Hz, 2 H), 2.76 (q, J=7.8 Hz, 2 H), 3.91 (q, J=7.8 Hz, 2 H), 4.40 (q, J=7.8 Hz, 2 H). HRMS: calcd for C$_{20}$H$_{29}$NO$_3$S 363.1868, found 363.1858.

5-Ethyl 2,4-diethyl-3-(propylsulfanylcarbonyl)-6-phenylpyridine-5-carboxylate (53)

$^1$H NMR d: 0.98 (t, J=7.8 Hz, 3 H), 1.07 (t, J=7.8 Hz, 3 H), 1.23 (t, J=7.8 Hz, 3 H), 1.34 (t, J=7.8 Hz, 3 H), 1.76 (m, 2 H), 2.73 (q, J=7.8 Hz, 2 H), 2.87 (q, J=7.8 Hz, 2 H), 3.12 (q, J=7.8 Hz, 2 H), 4.10 (q, J=7.8 Hz, 2 H), 7.42–7.43 (m, 3 H), 7.58–7.61 (m, 2 H). MS (CI/NH$_3$): m/z 386 (M$^+$+1, base).

5-Propyl 2,4-diethyl-3-(propylsulfanylcarbonyl)-6-(m-chlorophenyl)pyridine-5-carboxylate (54)

$^1$H NMR d: 0.72 (t, J=7.8 Hz, 3 H), 1.07 (t, J=7.8 Hz, 3 H), 1.23 (t, J=7.8 Hz, 3 H), 1.34 (t, J=7.8 Hz, 3 H), 1.46 (m, 2 H), 1.77 (m, 2 H), 2.72 (q, J=7.8 Hz, 2 H), 2.86 (q, J=7.8 Hz, 2 H), 3.13 (t, J=6.9 Hz, 2 H), 4.04 (t, J=6.9 Hz, 2 H), 7.37 (m, 2 H), 7.48 (m, 1 H), 7.62 (s, 1 H). MS (CI/NH$_3$): m/z 434 (M$^+$(C$_{23}$H$_{28}$$^{35}$ClNO$_3$S)+1, base), 404 (M$^+$–C$_2$H$_5$), 358 (M$^+$–PrS).

5-Ethyl 2-propyl-4-ethyl-3-(ethylsulfanylcarbonyl)-6-phenylpyridine-5-carboxylate (55)

$^1$H MNR d: 0.99 (t, J=6.9 Hz, 6 H), 1.23 (t, J=7.8 Hz, 3 H), 1.41 (t, J=7.8 Hz, 3 H), 1.82 (m, 2 H), 2.72 (q, J=6.9 Hz, 2 H), 2.81 (q, J=6.9 Hz, 2 H, 3.14 (q, J=7.8 Hz, 2 H), 4.10 (q, J=7.8 Hz, 2 H), 7.40–7.44 (m, 3 H), 7.57–7.60 (m, 2 H). MS (EI): m/z 385 (M$^+$), 340 (M$^+$–OEt), 324 (M$^+$–SEt), 296 (M$^+$–COSEt).

5-Ethyl 2-(2-methoxylethyl)-4-ethyl-3-(ethylsulfanylcarbonyl)-6-phenylpyridine-5-carboxylate (56)

$^1$H NMR d: 0.99 (t, J=7.8 Hz, 3 H), 1.23 (t, J=7.8 Hz, 3 H), 1.41 (t, J=7.8 Hz, 3 H), 2.73 (q, J=7.8 Hz, 2 H), 3.11–3.18 (m, 4 H), 3.37 (s, 3 H), 3.8 (t, J=7.8 Hz, 2 H), 4.10 (q, J=7.8 Hz, 2 H), 7.42–7.44 (m, 3 H), 7.5 8–7.61 (m, 2 H). MS (CI/NH$_3$): m/z 402 (MH$^+$, base). HRMS: calcd. for CH$_{22}$H$_{27}$NO$_4$S 401.1661, found 401.1666.

5-Ethyl 2-butyl-4-ethyl-3-(ethylsulfanylcarbonyl)-6-phenylpyridine-5-carboxylate (57)

$^1$H NMR d: 0.93 (t, J=7.8 Hz, 3 H), 0.99 (t, J=7.8 Hz, 3 H), 1.23 (t, J=7.8 Hz, 3 H), 1.28–1.39 (m, 2 H), 1.41 (t, J=7.8 Hz, 3 H), 1.77 (m, 2 H), 2.72 (q, J=7.8 Hz, 2 H), 2.83 (t, J=7.8 Hz, 2 H), 3.13 (q, J=7.8 Hz, 2 H), 4.10 (q, J=7.8 Hz, 2 H), 7.40–7.43 (m, 3 H), 7.58–7.60 (m, 2 H). MS(CI/NH$_3$): m/z 400 (M$^+$+1, base). MS (EI): m/z 400 (M$^+$+1), 371 (MH$^+$–Et), 338 (M$^+$–SEt, base). HRMS: calcd. for C$_{23}$H$_{29}$NO$_3$S 399.1868, found 399.1867.

5-Ethyl 2-cyclobutyl-4-ethyl-3-(ethylsulfanylcarbonyl)-6-phenylpyridine-5-carboxylate (58)

$^1$H NMR d: 1.00 (t, J=7.8 Hz, 3 H), 1.21 (t, J=7.8 Hz, 3 H), 1.42 (t, J=7.8 Hz, 3 H), 1.86–1.95 (m, 1 H), 1.95–2.05 (m, 1 H), 2.17–2.56 (m, 2 H), 2.51–2.64 (m, 2 H), 2.70 (q, J=7.8 Hz, 2 H), 3.13 (q, J=7.8 Hz, 2 H), 3.79 (m, 1 H), 4.11 (q, J=7.8 Hz, 2 H), 7.42–7.44 (m, 3 H), 7.67–7.69 (m, 2 H). MS(CI/NH$_3$): m/z 398 (M$^+$+1, base).

EXAMPLE 6

This Example illustrates the analytical data of dihydropyridines and pyridines of the present invention. The elemental analysis, the mass spectral data and the yield data obtained are set forth in Table 1.

TABLE 1

The elemental analysis, high resolution mass spectra (HRMS), and the synthetic yield data for certain dihydropyridine and pyridine derivatives.

| Compound | Formula | MW | Calculated (%) | | | Found (%) | | | Yield (%) |
|---|---|---|---|---|---|---|---|---|---|
| | | | C | H | N | C | H | N | |
| 60 | C$_{20}$H$_{25}$NO$_4$ + 0.25H$_2$O | 343.41 | 69.04 | 7.39 | 4.04 | 68.72 | 7.21 | 3.94 | 63 |
| 61 | C$_{20}$H$_{25}$NO$_4$ | 343.41 | 69.95 | 7.34 | 4.08 | 69.65 | 7.39 | 3.99 | 55 |
| 62 | C$_{20}$H$_{25}$NO$_3$S | 359.48 | 66.82 | 7.01 | 3.90 | 66.78 | 7.08 | 3.80 | 81 |
| 63 | C$_{21}$H$_{27}$NO$_4$S | 389.50 | 64.75 | 6.99 | 3.60 | 64.72 | 7.16 | 3.43 | 68 |
| 64 | C$_{21}$H$_{27}$NO$_3$S + 0.1H$_2$O | 375.31 | 67.20 | 7.31 | 3.58 | 67.11 | 7.39 | 3.58 | 54 |
| 65 | C$_{25}$H$_{27}$NO$_3$S | 421.54 | 71.23 | 6.46 | 3.32 | 71.11 | 6.43 | 3.40 | 47 |
| 66 | C$_{21}$H$_{27}$NO$_6$ | 389.44 | 64.76 | 6.99 | 3.60 | 66.58 | 6.25 | 3.97 | 30 |
| 67[a] | C$_{19}$H$_{21}$NO$_5$ | 343.37 | HRMS (M$^+$–CHO): 314.1392 | | | 314.1432 | | | 82 |
| 70 | C$_{28}$H$_{27}$NO$_4$ + 0.5C$_3$H$_6$O | 470.54 | 75.29 | 6.43 | 2.98 | 75.32 | 6.31 | 3.31 | 24 |

TABLE 1-continued

The elemental analysis, high resolution mass spectra (HRMS), and the synthetic yield data for certain dihydropyridine and pyridine derivatives.

| Compound | Formula | MW | Calculated (%) C | H | N | Found (%) C | H | N | Yield (%) |
|---|---|---|---|---|---|---|---|---|---|
| 71 | $C_{29}H_{29}NO_4 + 0.2H_2O$ | 459.13 | 75.86 | 6.45 | 3.05 | 75.95 | 6.48 | 3.01 | 35 |
| 72 | $C_{30}H_{31}NO_4$ | 469.56 | 76.73 | 6.65 | 2.98 | 76.46 | 6.60 | 2.83 | 16 |
| 73 | $C_{31}H_{33}NO_4$ | 483.60 | 76.99 | 6.88 | 2.90 | 76.73 | 6.97 | 2.86 | 52 |
| 74 | $C_{20}H_{25}NO_4$ | 343.41 | 69.95 | 7.34 | 4.08 | 69.99 | 7.42 | 4.05 | 58 |
| 75 | $C_{21}H_{27}NO_3S$ | 373.51 | 67.52 | 7.29 | 3.75 | 67.44 | 7.37 | 3.59 | 72 |
| 76 | $C_{22}H_{29}NO_3S$ | 387.53 | 68.18 | 7.54 | 3.61 | 68.17 | 7.32 | 3.60 | 45 |
| 34[b] | $C_{20}H_{23}NO_4$ | 341.39 | HRMS(M+): 341.1627 | | | 341.1635 | | | 78 |
| 35[c] | $C_{20}H_{23}NO_4$ | 341.39 | HRMS(M+): 341.1627 | | | 341.1615 | | | 85 |
| 36 | $C_{20}H_{23}NO_3S$ | 357.46 | 67.20 | 6.49 | 3.92 | 67.13 | 6.58 | 4.32 | 61 |
| 37 | $C_{21}H_{25}NO_4S$ | 387.48 | 65.09 | 6.50 | 3.62 | 65.11 | 6.71 | 3.54 | 65 |
| 38 | $C_{21}H_{25}NO_3S$ | 371.49 | 67.89 | 6.78 | 3.77 | 68.01 | 6.75 | 3.66 | 78 |
| 39 | $C_{25}H_{25}NO_3S$ | 419.53 | 71.57 | 6.01 | 3.34 | 71.30 | 6.11 | 3.23 | 82 |
| 40[d] | $C_{21}H_{25}NO_6$ | 387.42 | HRMS(M+): 387.1682 | | | 387.1674 | | | 59 |
| 41 | $C_{19}H_{19}NO_5 + 0.4C_7H_8$ | 378.21 | 70.25 | 6.05 | 3.53 | 70.18 | 6.01 | 4.20 | 55 |
| 44 | $C_{29}H_{27}NO_4$ | 453.51 | 76.80 | 6.00 | 3.09 | 76.61 | 6.09 | 3.04 | 83 |
| 45 | $C_{30}H_{29}NO_4$ | 467.54 | 77.06 | 6.25 | 3.00 | 77.03 | 6.26 | 2.98 | 34 |
| 46[e] | $C_{20}H_{23}NO_4$ | 341.39 | HRMS(M+): 341.1627 | | | 341.1631 | | | 96 |
| 47 | $C_{18}H_{19}NO_4 + 0.1C_7H_8$ | 322.56 | 69.63 | 6.19 | 4.34 | 69.94 | 6.58 | 4.10 | 56 |
| 48 | $C_{21}H_{25}NO_3S$ | 371.49 | 67.89 | 6.78 | 3.77 | 68.07 | 6.94 | 3.66 | 39 |
| 49a | $C_{22}H_{27}NO_3S$ | 385.52 | 68.54 | 7.06 | 3.63 | 70.16 | 7.25 | 3.35 | 85 |
| 49b | $C_{23}H_{29}NO_3S$ | 399.54 | 69.14 | 7.32 | 3.51 | 68.86 | 7.25 | 3.61 | 71 |
| 50 | $C_{21}H_{25}NO_4S$ | 387.49 | 65.09 | 6.50 | 3.62 | 64.91 | 6.47 | 3.46 | 54 |
| 51 | $C_{21}H_{24}ClNO_3S + 0.1C_7H_8$ | 415.14 | 62.78 | 5.85 | 3.37 | 62.98 | 6.04 | 3.23 | 58 |
| 52[f] | $C_{20}H_{29}NO_3S$ | 363.51 | HRMS(M+): 363.1868 | | | 363.1858 | | | 52 |
| 53 | $C_{22}H_{27}NO_3S + 0.1H_2O$ | 387.32 | 68.22 | 7.08 | 3.62 | 68.14 | 7.15 | 3.53 | 79 |
| 54 | $C_{23}H_{28}ClNO_3S$ | 433.98 | 63.65 | 6.50 | 3.23 | 63.40 | 6.53 | 3.08 | 65 |
| 55 | $C_{22}H_{27}NO_3S$ | 385.51 | 68.54 | 7.06 | 3.63 | 68.48 | 7.33 | 3.41 | 51 |
| 56[g] | $C_{22}H_{27}NO_4S$ | 401.51 | HRMS(M+): 401.1661 | | | 401.1666 | | | 65 |
| 57[h] | $C_{23}H_{29}NO_3S$ | 399.54 | HRMS(M+): 399.1868 | | | 399.1867 | | | 53 |
| 58 | $C_{23}H_{27}NO_3S + 0.6H_2O$ | 408.33 | 67.65 | 6.96 | 3.43 | 67.77 | 6.70 | 3.23 | 64 |

The following compounds were shown to be pure on analytical TLC (silica gel 60, 250 μm) EtOAc-Petroleum ether = 10:90 (v/v), unless otherwise noted. The $R_f$ values are set forth below:
[a]Compound 67, $R_f$ = 0.87
[b]Compound 34, $R_f$ = 0.44
[c]Compound 35, $R_f$ = 0.35
[d]Compound 40, EtOAc-petroleum ether = 20:80 (v/v), $R_f$ = 0.36
[e]Compound 46, $R_f$ = 0.46
[f]Compound 52, $R_f$ = 0.51
[g]Compound 56, $R_f$ = 0.27
[h]Compound 57, $R_f$ = 0.54

EXAMPLE 7

Figure 6:
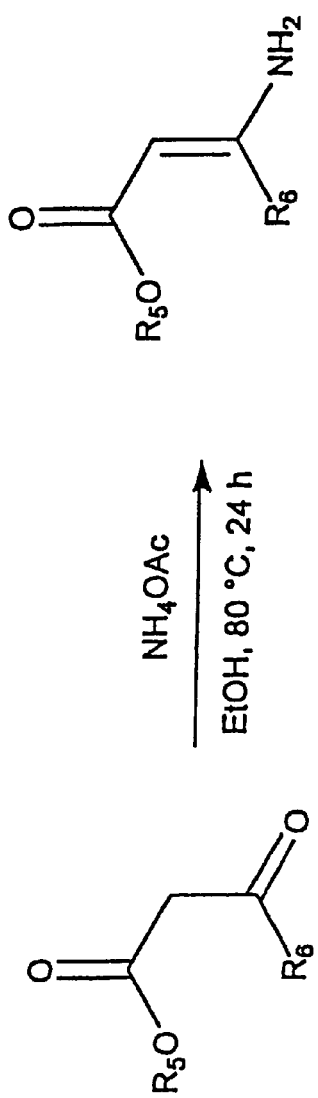
FIG. 6 depicts a method of synthesis of β-enaminoesters 77a, 77b, and 77d–h.
Figure 7:
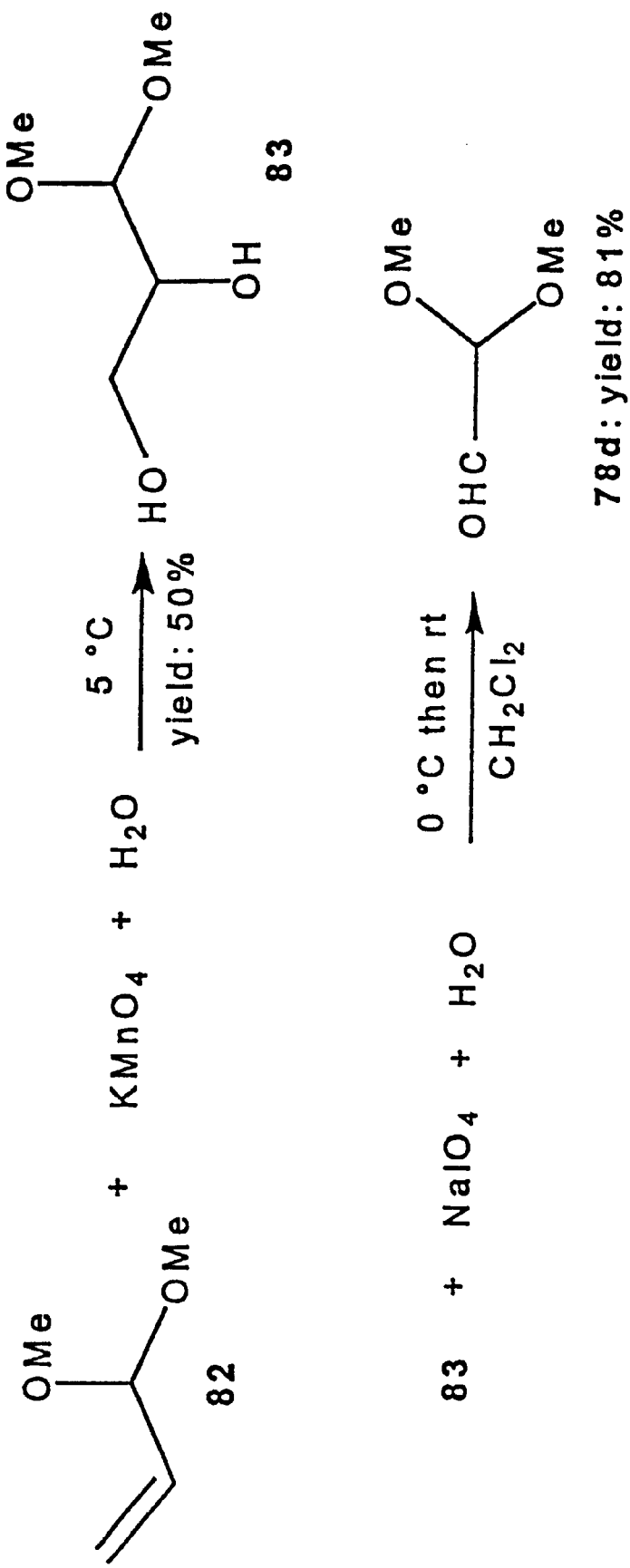
FIG. 7 depicts a method of synthesis of 2, 2-dimethoxy acetaldehyde (78d).

This Example illustrates a procedure for the preparation of β-amino-α,β-unsaturated esters which are intennediates in the synthesis of the pyridines and dihydropyridines of the present invention. The reactions involved are schematically shown in FIG. 6.

A β-ketoester (3 mmol) and ammonium acetate (4.5 mmol) were mixed in 5 mL of absolute ethanol and refluxed at 80° C. for 24 h. The solvent was removed, and the residue was chromatographed to give the desired compounds in moderate yields. The $^1$HNMR and high resolution mass spectral data of the β-enaminoesters are set forth below.

Ethyl 3-amino-3-phenyl-2-propenoate (77a)

$^1$H NMR d: 1.30 (t, J=6.9 Hz, 3 H), 4 18 (q, J=6.9 Hz, 2 H) 4.97 (s, 1 H), 7.41–7.53 (m, 3 H), 7.54–7.57 (m, 2 H).

Benzyl 3-amino-3-phenyl-2-propenoate (77b)

$^1$H NMR d: 4.97 (s, 1/4 H), 5.05 (s, 3/4 H), 5.18 (s, 2 H), 7.29–7.56 (m, 10 H). MS(CI/NH$_3$): m/z 272 (M$^+$+NH$_4$), 254 (M$^+$+1, base).

Propyl 3-amino-3-phenyl-2-propenoate (77d)

$^1$H NMR d: 0.98 (t, J=7.8 Hz, 3 H), 1.70 (m, 2 H), 4.09 (t, J=7.8 Hz, 2 H), 4.99 (s, 1 H), 7.39–7.44 (m, 3 H), 7.54–7.57 (m, 2 H). MS(CI/NH$_3$): m/z 206 (M$^+$+1, base).

Hydroxyethyl 3-amino-3-phenyl-2-propenoate (77e)

$^1$H NMR d: 3.87 (m, 2 H), 4.28 (m, 2 H), 5.02 (s, 1 H), 7.43–7.47 (m, 3 H), 7.54–7.57 (m, 2 H). MS(CI/NH$_3$): m/z 208 (M$^+$+1, base), 192 (M$^+$–NH$_2$).

Ethyl 3-amino-3-(m-chlorophenyl)-2-propenoate (77f)

$^1$H NMR d: 1.30 (t, J=6.9 Hz, 3 H), 4.18 (q, J=6.9 Hz, 2 H), 4.95 (s, 1 H), 7.35–7.44 (m, 3 H), 7.54 (s, 1 H). MS(CI/NH$_3$): m/z 226 ($C_{11}H_{12}{}^{35}ClNO_2$, M$^+$+1, base), 227 (M$^+$, $C_{11}H_{12}{}^{37}ClNO_2$).

Ethyl 3-amino-3-cyclopentyl-2-propenoate (77g)

$^1$H NMR d: 1.27 (t, J=6.9 Hz, 3 H), 1.54–1.81 (m, 6 H), 1.89–1.94 (m, 2 H), 2.50 (m, 1 H), 4.11 (q, J=6.9 Hz, 2 H), 4.60 (s, 1 H). MS(CI/NH$_3$): m/z 184 (M$^+$+1, base).

Propyl 3-amino-3-(m-chlorophenyl)-2-propenoate (77h)

$^1$H NMR d: 0.98 (t, J=6.9 Hz, 3 H), 1.69 (m, 2 H), 4.09 (q, J=6.9 Hz, 2 H), 4.96 (s. 1 H), 7.32– 7.45 (m, 3 H), 7.54 (s, 1 H). MS(CI/NH$_3$): m/z 240 ($C_{12}H_{14}{}^{35}ClNO_2$, M$^+$+1, base). MS(EI): m/z 239 (M$^+$), 223 (M$^+$–NH$_2$), 180 (M$^+$–PrO), 153 (M$^+$–1–CO$_2$Pr, base).

EXAMPLE 8

This Example illustrates a method of preparation of 2,2-dimethoxyacetaldehyde (78d), which is an intermediate in the preparation of the pyridines and dihydropyridines of the present invention. This compound was prepared using a published procedure with some modifications. E. J. Witzemann et al., Org. Synth. Coll. II, 307–308 (1943).

Potassium permanganate (16 g, 100 mmol) in 300 mL of water was added slowly to a vigorously stirred ice-cooled suspension of 10.2 g (100 mmol) of acrolein dimethyl acetal in 120 mL of water. The speed of addition was controlled to keep the temperature as near to 5° C. as possible. Soon after the stirring stopped, the mixture formed a gel. After standing for 2 h, the mixture was heated at 95° C. for 1 h and then filtered. Upon cooling, the filtrate was treated with 240 g of anhydrous $K_2CO_3$. The organic phase was separated, and the aqueous phase was extracted with ethyl acetate (80 mL×5). Organic phases were combined and dried with anhydrous $MgSO_4$. After removing the solvent, a colorless oil (6.84 g, yield: 50%) remained which was identified as dl-glyceraldehyde dimethyl acetal (83): $^1$H NMR d: 2.44 (s, br, 1 H), 2.73 (s, br, 1 H), 3.48 (s, 6 H), 3.69–3.73 (m, 3 H), 4.36 (d, J=6.0 Hz, 1 H). MS(CI/$NH_3$): m/z 154 ($M^+$+$NH_4$, base).

Compound 83 (2.11 g, 15.5 mmol) was dissolved in a mixture of dichloromethane (100 mL) and water (5 mL), and cooled to 0° C. While stirring, sodium periodate (7.5 g, 35 mmol) was carefully added in three portions within 30 min. After stirring for an additional 1 h at room temperature, anhydrous $MgSO_4$ (14 g) was added to the reaction mixture, and stirring was continued for an additional 0.5 h. The reaction was then filtered. Removal of the solvent left 1.38 g of the desired product 78d, yield: 85%. $^1$H NMR: δ3.46 (s, 6 H), 4.50 (d, J=1.8 Hz, 1 H), 9.48 (d, J=1.8 Hz, 1 H).

EXAMPLE 9

Figure 8:
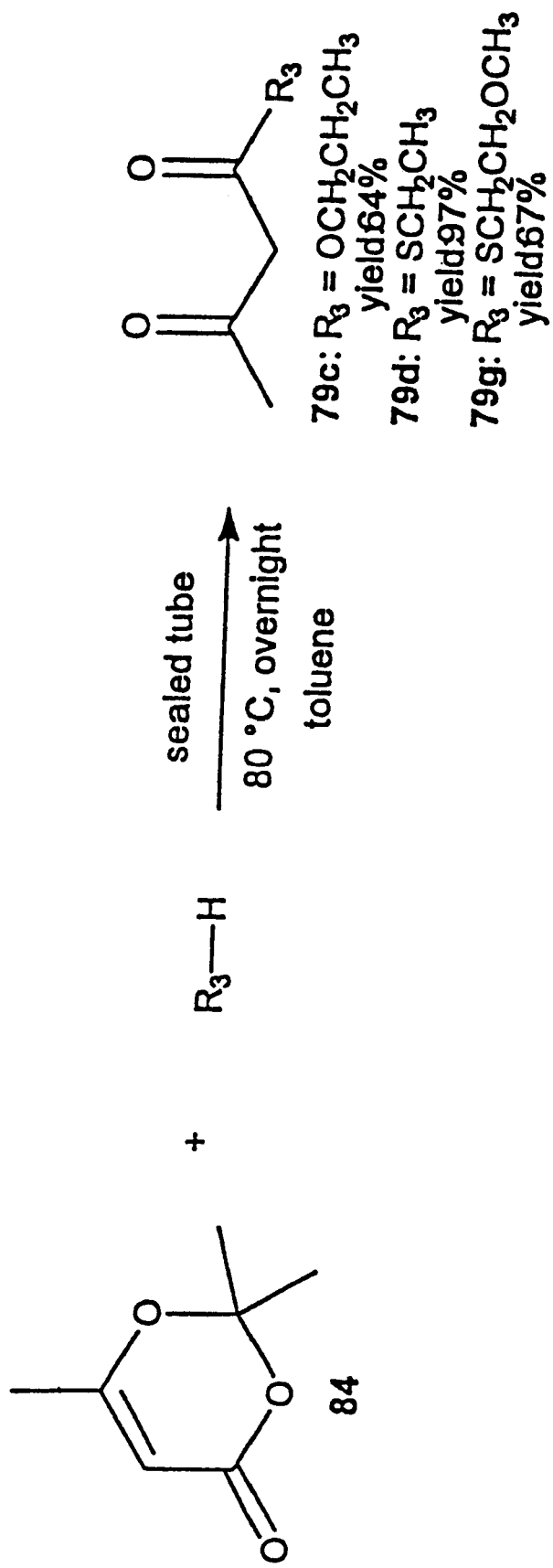
FIG. 8 depicts a method of synthesis of β-ketoesters 79c, 79d, and 79g.

This Example illustrates a method for the synthesis of β-ketoesters 79c, 79d, 79g, 79j–k, and 79u which are intermediates in the preparation of pyridines and dihydropyridines of the present invention. β-Ketoester 79c and β-ketothioesters 79d and 79g were prepared by the reaction of 2,2,6-trimethyl-4H-1,3-dioxin-4-one (84) and an alcohol or a thiol, shown schematically in FIG. 8. Equimolar amounts (for example, 3 mmol) of compound 84 and an alcohol or a thiol were heated with a little toluene (1–2 mL) at 100° C. in a sealed tube overnight. After being cooled to room temperature, the solvent was removed under reduced pressure and the residue was chromatographed to give the desired products in satisfactory yields (64% for 79c, 97% for 79d, and 67% for 79g). The NMR and mass spectral data are set forth below.

Propyl acetoacetate (79c)

$^1$H NMR d: 0.94 (t, J=6.9 Hz, 3 H), 1.66 (m, 2 H), 2.27 (s, 3 H), 3.46 (s, 2 H), 4.09 (t, J=6.9 Hz, 2 H).

S-Ethyl 3-oxothiobutyrate (79d)

$^1$H NMR d: 1.28 (t, J=7.8 Hz, 3 H), 2.27 (s, 3 H), 2.94 (q, J=7.8 Hz, 2 H), 3.67 (s, 2 H).

S-(2-Methoxyethyl) 3-oxothiobutyrate (79g)

Figure 9:
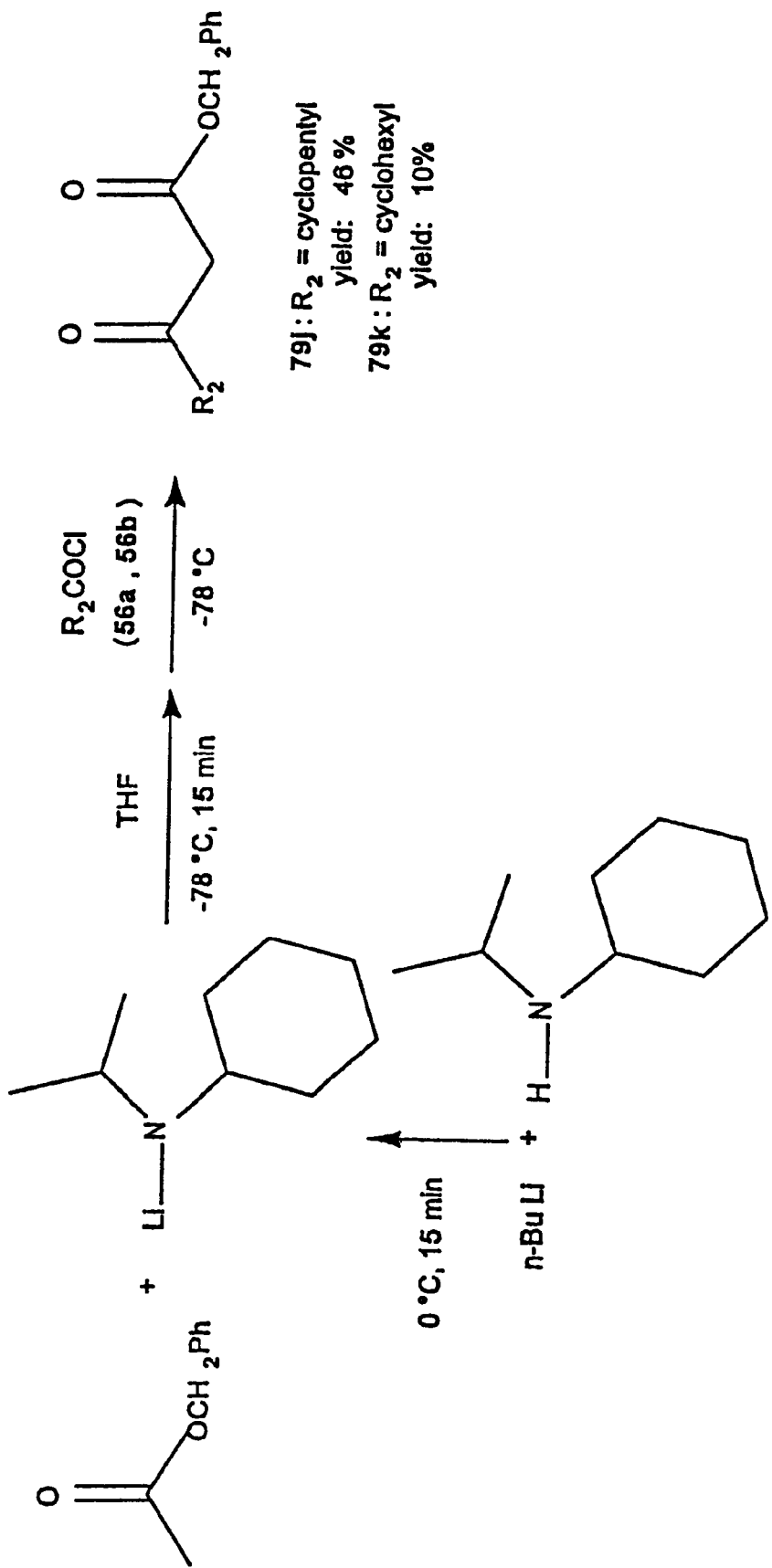
FIG. 9 depicts a method of synthesis of β-ketoesters 79j and 79k.

$^1$H NMR d: 2.27 (s, 3 H), 3.15 (t, J=6.0 Hz, 2 H), 3.37 (s, 3 H), 3.55 (t, J=6.0 Hz, 2 H), 3.69 (s, 2 H). MS (CI/$NH_3$): 194 ($M^+$+$NH_4$, base), 176 ($M^+$).

β-Ketoesters 79j and 79k were prepared by a route shown schematically in FIG. 9. N-Isopropylcyclohexylamine (0.786 g, 5.5 mmol) and n-BuLi (2.2 mL, 5.5 mmol, 2.5 N in hexanes) were mixed at 0° C. in 15 mL of THF for 15 min. The temperature was then lowered to −78° C. Benzyl acetate (0.752 g, 0.72 mL, 5 mmol) was then added slowly into this system and stirred for 10 min at the same temperature to form an enolate. Cyclohexanecarbonyl chloride (0.806 g, 0.74 mL, 5.5 mL, for 79k) or cyclopentanecarbonyl chloride (0.729 g, 0.67 mL, 5.5 mmol, for 79j) was added dropwise to this enolate solution within 10 min. After stirring for 15 min, the reaction mixture was allowed to warm to room temperature and poured into 10 mL of 1 N HCl. The organic phase was separated, and the aqueous phase was extracted with ether (10 mL×3). The combined organic phases were washed with 1 N $NaHCO_3$ (10 ml) and water (10 mL), and then dried with arhydrous $MgSO_4$. The solvent was removed, and the residue was chromatographed (silica 60, petroleum ether-ethyl acetate (9:1)) to give 130 mg of 79k (yield: 10%) or 569 mg of 79j (yield: 46%). The NMR data are set fort below.

Benzyl 3-oxo-3-clopentylpropionate (79j)

$^1$H NMR d: 1.19–1.81 (m, 8 H), 2.76–2.85 (m, 1 H), 3.55 (s, 2 H), 5.11 (s, 2 H), 7.31–7.36 (m, 5 H).

Benzyl 3-oxo-3-cyclohexylproionate (79k)

$^1$H NMR d: 1.20–1.51 (m, 5 H), 1.66–1.96 (m, 5 H), 2.25–2.38 (m, 1 H), 3.51 (s, 2 H), 5.19 (s, 2 H), 7.37 (m, 5 H).

Figure 10:
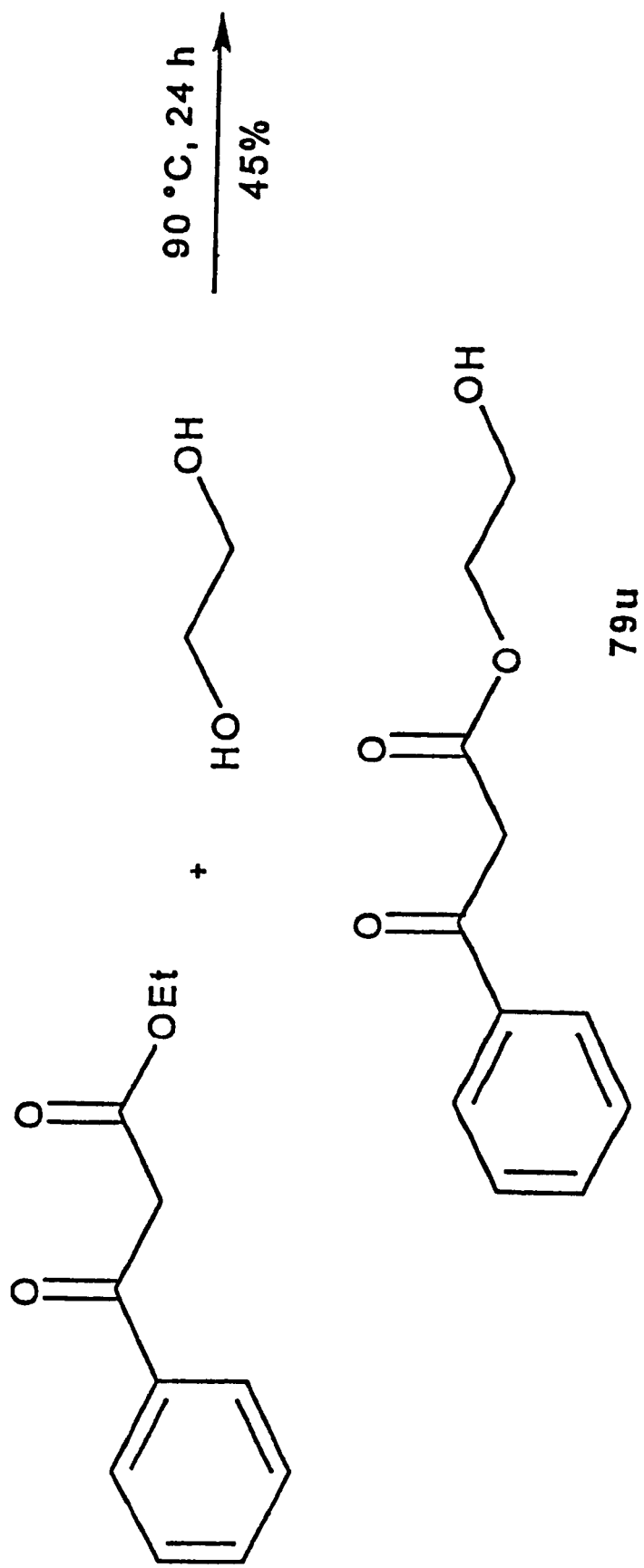
FIG. 10 depicts a method of synthesis of β-ketoester 79u.

To prepare compound 79u, a transesterification reaction shown schematically in FIG. 10 was used. Ethyl benzoylacetate (1.92 g, 10 mmol) and ethylene glycol (0.621 g, 10 mmol) in toluene (10 mL) were heated with stirring for 24 h. The solvent was removed, and the residue was chromatographed (silica 60, petroleum ether-ethyl acetate (3:1)) to give 0.946 g of the desired product, yield: 45%. The $^1$HNMR data are set forth below.

Hydroxyethyl benzoylacetate (79u)

$^1$H NMR d: 2.52 (s, br, 1 H), 3.4 (m, 2 H), 4.08 (s, 2 H), 4.35 (t, J=7.8 Hz, 2 H), 7.43–7.53 (m, 2 H), 7.60–7.65 (m, 1 H), 7.93–7.96 (m, 2 H).

EXAMPLE 10

Figure 11:
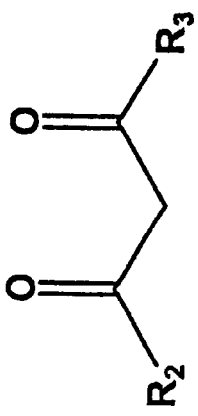
FIG. 11 depicts a method of synthesis of β-ketoesters 79e, 79f, 79h, 79i, 79l–n, and 79p–t.
Figure 11:
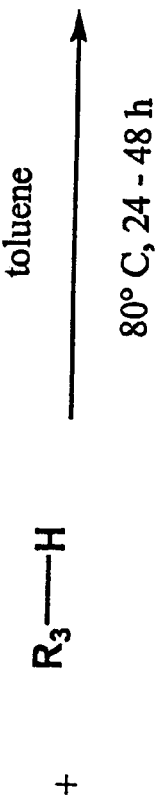

This Example illustrates a method of preparation of the β-ketoesters 79e–f, 79h–i, 79e–n, and 79p–t via Meldrum's acids, shown schematically in FIG. 11. Oikawa et al., J. Org. Chem., 43, 2087–2088 (1978).

The preparation of S-ethyl 3-oxothiovalerate (79e) is provided here as an example. 2,2-Dimethyl-1,3-dioxane-4, 6-dione (86, 0.721 g, 5 mmol) and propionyl chloride (0.509 g, 5.5 mmol) were dissolved in 10 mL of dry $CH_2Cl_2$. At 0° C., 0.81 mL (0.791 g, 10 mmol) of pyridine (in the cases of aromatic acid chlorides, using 4-dimethylaminopyridine instead of pyridine) was then added dropwise. The reaction temperature was kept at 0° C. for 1 h, and then raised to room temperature for an additional 1 h. The reaction mixture was then washed with 1 N HCl (10 mL) and water (5 mL), and then dried with anhydrous $MgSO_4$. Removal of the solvent yielded the desired product (87e), which was directly used for the next reaction without further purification.

Compound 87e (670 mg, 3.35 mmol) and ethanethiol (0.621 g, 10 mmol) were mixed in 10 mL of toluene. This mixture was heated at 80° C. in a flask with an effective flux condenser for 24 h. The solvent and excess ethanethiol were removed, and the residue was chromatographed (silica 60, petroleum ether-ethyl acetate (9:1)) to give the desired product 282 mg, yield: 53%. The NMR and mass spectral data are set forth below:

S-Ethyl 3-oxothiovalerate (79e)

$^1$H NMR d: 1.07 (t, J=6.9 Hz, 3 H), 1.28 (t, J=6.9 Hz, 3 H), 2.58 (q, J=6.9 Hz, 2 H), 2.94 (q, J=6.9 Hz, 2 H), 3.66 (s, 2 H). MS (CI/NH$_4$): m/z 178 (M$^+$+NH$_4$), 161 (M$^+$+1).

S-Ethyl 3-oxothiocaproate (79f)

$^1$H NMR d: 0.92 (t, J=7.8 Hz, 3 H), 1.28 (t, J=7.8 Hz, 3 H), 1.62 (m, 2 H), 2.53 (t, J=6.9 Hz, 2 H), 2.93 (q, J=7.8 Hz, 2 H), 3.65 (s, 2 H). MS (CI/NH$_4$): m/z 192 (M$^+$+NH$_4$, base), 175 (M$^+$+1).

Benzyl 3-oxo-3-cyclopropylpropionate (79h)

$^1$H NMR d: 0.90–0.96 (m, 2 H), 1.08–1.13 (m, 2 H), 1.98–2.05 (m, 1 H), 3.62 (s, 2 H), 5.20 (s, 2 H), 7.30–7.39 (m, 5 H). MS (CI/NH$_4$): m/z 236 (M$^+$+NH$_4$, base), 219 (M$^+$+1).

Benzyl 3-oxo-3-cyclobutylpropionate (79i)

$^1$H NMR d: 1.59–2.37 (m, 6 H), 3.37 (m, 1 H), 3.45 (s, 2 H), 5.17 (s, 2 H), 7.34–7.37 (m, 5 H). MS (CI/NH$_4$): m/z 250 (M$^+$+NH$_4$, base), 233 (M$^+$+1).

S-Ethyl 3-oxothioheptanoate (79 l)

$^1$H NMR d: 0.91 (t, J=7.8 Hz, 3 H), 1.28 (t, J=7.8 Hz, 3 H), 1.51–1.62 (m, 4 H), 2.55 (t, J=7.8 Hz, 2 H), 2.93 (q, J=7.8 Hz, 2 H), 3.65 (s, 2 H). MS (CI/NH$_4$): m/z 206 (M$^+$+NH$_4$, base).

S-Propyl 3-oxothiovalerate (79m)

$^1$H NMR d: 0.98 (t, J=6.9 Hz, 3 H), 1.07 (t, J=7.8 Hz, 3 H), 1.62 (m, 2 H), 2.58 (q, J=6.9 Hz, 2 H), 2.91 (t, J=7.8 Hz, 2 H), 3.67 (s, 2 H). MS (CI/NH$_4$): m/z 175 (M$^+$+1).

S-Ethyl 3-oxo-3-cyclobutylthiopropionate (79n)

$^1$H NMR d: 1.27 (t, J=7.8 Hz, 3 H), 1.85 (m, 1 H), 1.93–2.05 (m, 1 H), 2.14–2.31 (m, 4 H), 2.92 (q, J=7.8 Hz, 2 H), 3.42 (m, 1 H), 3.61 (s, 2 H). MS (CI/NH$_4$): m/z 204 (M$^+$+NH$_4$, base), 187 (M$^+$+1).

S-Ethyl 3-oxo-5-methoxythiovalerate (79p)

$^1$H NMR d: 1.28 (t, J=7.8 Hz, 3 H), 2.80 (t, J=6.0 Hz, 2 H), 2.93 (q, J=7.8 Hz, 2 H), 3.34 (s, 3 H), 3.65 (t, J=6.0 Hz, 2 H), 3.71 (s, 2 H). MS (CI/NH$_4$): m/z 208 (M$^+$+NH$_4$, base), 191 (M$^+$+1).

Ethyl 3-oxo-3-cyclopentylpropionate (79q)

$^1$H NMR d: 1.28 (t, J=7.8 Hz, 3 H), 1.59–1.71 (m, 2 H), 1.76–1.88 (m, 2 H), 2.98 (m, 1 H), 3.49 (s, 2 H), 4.19 (q, J=7.8 Hz, 2 H). MS (CI/NH$_4$): m/z 202 (M$^+$+NH$_4$, base).

Propyl benzoylacetate (79r)

$^1$H NMR d: 0.95 (t, J=6.9 Hz, 3 H), 1.64–1.71 (m, 2 H), 3.39 (s, 2 H), 4.12 (t, J=6.9 Hz, 2 H), 7.47–7.97 (m, 5 H). MS (CI/NH$_4$): m/z 224 (M$^+$+NH$_4$, base), 206 (M$^+$).

Ethyl m-chlorobenzoylacetate (79s)

$^1$H NMR d: 1.26 (t, J=6.9 Hz, 3 H), 3.91 (s, 2 H), 4.22 (t, J=6.9 Hz, 2 H), 7.36–7.84 (m, 3 H), 7.93 (s, 1 H). MS (CI/NH$_4$): m/z 244 (C$_{11}$H$_{11}$$^{35}$ClO$_3$, M$^+$+NH$_4$, base), 227 (C$_{11}$H$_{11}$$^{35}$ClO$_3$, M$^+$+1).

Propyl m-chlorobenzoylacetate (79t)

$^1$H NMR d: 0.90 (t, J=7.8 Hz, 3 H), 1.64 (m, 2 H), 3.98 (s, 2 H), 4.12 (t, J=6.9 Hz, 2 H), 7.36–7.84 (m, 3 H), 7.93 (s, 1 H). MS (CI/NH$_4$): m/z 258 (C$_{11}$H$_{11}$$^{35}$ClO$_3$, M$^+$+NH$_4$, base), 241 (C$_{11}$H$_{11}$$^{35}$ClO$_3$, M$^+$+1).

EXAMPLE 11

This Example illustrates the $A_1$, $A_2$, and $A_3$ adenosine receptor binding affinities of certain pyridine derivatives of the present invention. The affinities were determined in radioligand binding assays and the results thereof are set forth in Table 2.

TABLE 2

Affinities of Pyridine derivatives in radioligand binding assays at $A_1$, $A_{2A}$, and $A_3$ adenosine receptors.

| Compound | $R_2$ | $R_3$ | $R_4$ | $R_5$ | $R_6$ | $rA_1$ a | $rA_{2A}$ b | $hA_3$ c | $rA_1/hA_3$ |
|---|---|---|---|---|---|---|---|---|---|
| 1 | $CH_2CH_3$ | $SCH_2CH_3$ | $CH_2CH_3$ | $CH_2CH_3$ | Ph | $41 \pm 6\% (10^{-4})$ | $6130 \pm 1280$ | $20.0 \pm 1.9$ | >3000 |
| 2 | $CH_2CH_3$ | $SCH_2CH_3$ | $CH_2CH_2CH_3$ | $CH_2CH_3$ | Ph | $15600 \pm 6900$ | $2050 \pm 440$ | $18.9 \pm 4.1$ | 7400 |
| 3 | $CH_2CH_3$ | $SCH_2CH_3$ | $CH_2CH_3$ | $CH_2CH_2f$ | Ph | $11,500 \pm 2900$ | ~7000 | $4.22 \pm 0.66$ | 2700 |
| 4 | $CH_2CH_3$ | $SCH_2CH_3$ | $CH_2CH_2N$-Pth | $CH_2CH_3$ | Ph | $490 \pm 48$ | 4250 | $28\% (10^{-6})$ | 200 |
| 5 | $CH_2CH_3$ | $SCH_2CH_3$ | $CH_2CH_2N$-Pth | $CH_2CH_2CH_3$ | Ph | $5240 \pm 1760$ | d ($10^{-5}$) | $8.29 \pm 1.15$ | — |
| 6 | $CH_2CH_3$ | $SCH_2CH_3$ | $CH_2CH_3$ | $CH_2CH_2CH_3$ | 3-Cl—Ph | $7770 \pm 1830$ | d ($10^{-5}$) | $8.29 \pm 1.15$ | 8.20 |
| 7 | $CH_2CH_3$ | $S(CH_2)_2CH_3$ | $CH_2CH_3$ | $CH_2CH_2CH_3$ | Ph | $113,000 \pm 28,000$ | d ($10^{-5}$) | $18.9 \pm 4.1$ | 7400 |
| 8 | $CH_2CH_2OH$ | $SCH_2CH_3$ | $CH_2CH_3$ | $CH_2CH_2CH_3$ | Ph | $5940 \pm 930$ | ~20,000 | >100,000 | — |
| 9 | $CH_2CH_2OBn$ | $SCH_2CH_3$ | $CH_2CH_3$ | $CH_2CH_2CH_3$ | Ph | $16,000 \pm 1400$ | 7000 | $109 \pm 1$ | 160 |
| 10 | $CH_2CH_2F$ | $SCH_2CH_3$ | $CH_2CH_3$ | $CH_2CH_2CH_3$ | Ph | $19,800 \pm 1100$ | ~30,000 | 2.88 | — |
| 11 | $CH_2CH_2SCOCH_3$ | $SCH_2CH_3$ | $CH_2CH_3$ | $CH_2CR_2CH_3$ | Ph | $12,200 \pm 2200$ | 6000 | 8 | — |
| 12 | $CH_2CH_3$ | $SCH_2CH_2OH$ | $CH_2CH_3$ | $CH_2CH_2CH_3$ | Ph | $10,800 \pm 2800$ | $5590 \pm 2000$ | $51.1 \pm 13.3$ | 210 |
| 13 | $CH_2CH_3$ | $SCH_2CH_2OTHP$ | $CH_2CH_3$ | $CH_2CH_2CH_3$ | Ph | $18 \pm 1\% (10^{-4})$ | d ($10^{-4}$) | $517 \pm 151$ | >20 |
| 14 | $CH_2CH_3$ | $SCH_2$-(2,2-dimethyl-1,3-dioxolane) (rac) | $CH_2CH_3$ | $CH_2CH_2CH_3$ | Ph | $5710 \pm 1150$ | d ($10^{-4}$) | 3000 | — |
| 15 | $CH_2CH_3$ | $SCH_2CH_2F$ | $CH_2CH_3$ | $CH_2CH_2CH_3$ | Ph | $8220 \pm 3250$ | ~24,000 | $55.1 \pm 8.2$ | 150 |
| 16 | $CH_2CH_3$ | $SCH_2CF_3$ | $CH_2CH_3$ | $CH_2CH_2CH_3$ | Ph | $8290 \pm 2350$ | $6140 \pm 1850$ | $18.1 \pm 2.2$ | 460 |
| 17 | $CH_2CH_3$ | $SCH_2CH_2CH_2F$ | $CH_2CH_3$ | $CH_2CH_2CH_3$ | Ph | $12,600 \pm 2800$ | d ($10^{-4}$) | 1100 | — |
| 18 | $CH_2CH_3$ | $SCH_2CH_2OH$ | $CH_2CH_2OH_3$ | $CH_2CH_2CH_3$ | Ph | $9010 \pm 1890$ | — | 2200 | — |
| 19 | $CH_2CH_3$ | $SCH_2CH_3$ | $CH_2CH_2SCOCH_3$ | $CH_2CH_2CH_3$ | Ph | $9800 \pm 3490$ | 4000 | 100 | — |
| 20 | $CH_2CH_3$ | $SCH_2CH_3$ | $CH_2CH_2F$ | $CH_2CH_2CH_3$ | Ph | — | — | — | — |
| 21 | $CH_2CH_3$ | $SCH_2CH_3$ | $CH_2CH_2CH_2F$ | $CH_2CH_2CH_3$ | Ph | $8090 \pm 1040$ | 20,000 | 20 | — |
| 22 | $CH_2CH_3$ | $SCH_2CH_3$ | $CH_2CH_2CH_2OH$ | $CH_2CH_2CH_3$ | Ph | $9060 \pm 2350$ | $8760 \pm 2490$ | $169 \pm 61$ | 54 |
| 23 | $CH_2CH_3$ | $SCH_2CH_3$ | $CH_2CH_2CH_3$ | $CH_2CH_2CH_2F$ | Ph | $6050 \pm 1360$ | $9670 \pm 3340$ | $9.67 \pm 3.34$ | 630 |
| 24 | $CH_2CH_3$ | $SCH_2CH_3$ | $CH_2CH_2CH_3$ | $CH_2CF_2CF_3$ | 2-F-Ph | $5680 \pm 920$ | $15,400$ | $446 \pm 119$ | 13 |
| 25 | $CH_2CH_3$ | $SCH_2CH_3$ | $CH_2CH_2CH_3$ | $CH_2CH_2CH_3$ | 3-F-Ph | $13,500 \pm 1600$ | $8630 \pm 3550$ | $23.0 \pm 6.8$ | 590 |
| 26 | $CH_2CH_3$ | $SCH_2CH_3$ | $CH_2CH_2CH_3$ | $CH_2CH_2CH_3$ | 4-F-Ph | $8200 \pm 810$ | $28,100 \pm 10,900$ | $28.9 \pm 10.8$ | 280 |
| 27 | $CH_2CH_3$ | $SCH_2CH_3$ | $CH_2CH_2CH_3$ | $CH_2CH_2CH_3$ | Ph | $12,300$ | $50\% (10^{-4})$ | $31.1 \pm 9.24$ | ~400 |
| 28f | $CH_2CH_3$ | cyclized to $R_4$ as a lactone | $CH_2CH_2O—$ | $CH_2CH_2CH_3$ | Ph | $11,200 \pm 2500$ | 8000 | — | — |
| 29e | $CH_2CH_3$ | cyclized to $R_4$ as a lactone | $CH_2CH_2NH—$ | $CH_3$ | Ph | $5790 \pm 480$ | d ($10^{-4}$) | 2000 | — |
| 30e | $CH_2CH_3$ | cyclized to $R_4$ as a thiolactone | $CH_2CH_2S—$ | $CH_2CH_3$ | Ph | 26,000 | — | 200 | — |
| 31e | —$CH_2CH_2$— | cyclized to $R_2$ as thiolactone | $CH_2CH_2CH_3$ | $CH_2CH_3$ | Ph | $25,100 \pm 5900$ | — | $12\%(10^{-4})$ | — |
| 32e | | | | | | | | | |

TABLE 2-continued

Affinities of Pyridine derivatives in radioligand binding assays at $A_1$, $A_{2A}$, and $A_3$ adenosine receptors.

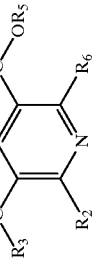

| Compound | $R_2$ | $R_3$ | $R_4$ | $R_5$ | $R_6$ | $rA_1$a | $rA_{2A}$b | $hA_3$c | $rA_1/hA_3$ |
|---|---|---|---|---|---|---|---|---|---|
| 33[e] | $CH_3$ | $OCH_2CH_3$ | $CH_3$ | $CH_2CH_3$ | Ph | 7.41 ± 1.29 | 28.4 ± 9.1 | 4.47 ± 0.46 | 1.7 |
| 34 | $CH_3$ | $OCH_2CH_2CH_3$ | $CH_3$ | $CH_2CH_3$ | Ph | 5.05 ± 0.54 | 24.5 ± 8.5 | 0.215 ± 0.022 | 23 |
| 35 | $CH_3$ | $OCH_2CH_3$ | $CH_2CH_3$ | $CH_2CH_3$ | Ph | 3.36 ± 0.60 | 3.69 ± 1.25 | 0.176 ± 0.038 | 19 |
| 36 | $CH_3$ | $SCH_2CH_3$ | $CH_2CH_3$ | $CH_2CH_3$ | Ph | 14.8 ± 3.5 | 14.9 ± 4.1 | 0.0429 ± 0.0088 | 340 |
| 37 | $CH_3$ | $SCH_2CH_2OCH_3$ | $CH_2CH_3$ | $CH_2CH_3$ | Ph | 36 ± 11% ($10^{-4}$) | 7.98 ± 1.36 | 0.165 ± 0.012 | >500 |
| 38 | $CH_3$ | $SCH_2CH_3$ | $CH_2CH_2CH_3$ | $CH_2CH_3$ | Ph | 29 ± 6% ($10^{-4}$) | 7.53 ± 2.70 | 0.194 ± 0.051 | >700 |
| 39 | $CH_3$ | $SCH_2CH_3$ | $CH(OCH_3)_2$ | $CH_2Ph$ | Ph | 20 ± 8% ($10^{-4}$) | 12.8 ± 2.9 | 2.61 ± 0.96 | >40 |
| 40 | $CH_3$ | $OCH_2CH_3$ | CHO | $CH_2CH_3$ | Ph | 1.95 ± 0.43 | 2.88 ± 0.61 | 0.783 ± 0.154 | 2.5 |
| 41 | $CH_3$ | $OCH_2CH_3$ | Ph—CH=CH— (trans) | $CH_2CH_3$ | Ph | 9.56 ± 4.09 | 2.56 ± 0.13 | — | — |
| 42 | $CH_3$ | $OCH_2CH_3$ | | $CH_2CH_3$ | Ph | 2.49 ± 0.47 | 2.40 ± 0.22 | 2.80 ± 1.78 | 0.85 |
| 43 | $CH_3$ | $OCH_2CH_3$ | Ph—C≡C— | $CH_2Ph$ | Ph | 11.6 ± 4.8 | 43 ± 20% ($10^{-4}$) | 2.75 ± 0.78 | 4.2 |
| 44 | $CH_3$ | $OCH_2CH_3$ | Ph—C≡C— | $CH_2Ph$ | cylobutyl | d ($10^{-4}$) | 27.6 ± 12.0 | 2.41 ± 0.59 | >40 |
| 45 | $CH_3$ | $OCH_2CH_3$ | Ph—C≡C— | $CH_2Ph$ | cyclopentyl | 56.2 ± 20.8 | 22.9 ± 5.0 | 3.85 ± 0.79 | 15 |
| 46 | $CH_2CH_3$ | $OCH_2CH_3$ | $CH_3$ | $CH_2CH_3$ | Ph | 10.3 ± 1.7 | 13.4 ± 4.2 | 0.121 ± 0.008 | 85 |
| 47 | $CH_2CH_3$ | OH | $CH_2CH_3$ | $CH_2CH_3$ | Ph | 4.25 ± 0.65 | 7.09 ± 0.97 | 30% ($10^{-4}$) | <1 |
| 48 | $CH_2CH_3$ | $SCH_2CH_3$ | $CH_2CH_3$ | $CH_2CH_3$ | Ph | 41 ± 6% ($10^{-4}$) | 6.13 ± 1.28 | 0.0200 ± 0.0019 | >3000 |
| 49a | $CH_2CH_3$ | $SCH_2CH_3$ | $CH_2CH_3$ | $CH_2CH_2CH_3$ | Ph | 7.77 ± 1.83 | d ($10^{-5}$) | 0.00829 ± 0.00115 | 940 |
| 49b | $CH_2CH_3$ | $SCH_2CH_3$ | $CH_2CH_2CH_3$ | $CH_2CH_3$ | Ph | 18.2 ± 9.0 | d ($10^{-4}$) | 0.0245 ± 0.0040 | 7400 |
| 50 | $CH_2CH_3$ | $SCH_2CH_3$ | $CH_2CH_2OH$ | $CH_2CH_3$ | Ph | 17.4 ± 5.29 | 10.0 ± 3.0 | 0.188 ± 0.061 | 93 |
| 51 | $CH_2CH_3$ | $SCH_2CH_3$ | $CH_2CH_3$ | $CH_2CH_3$ | 3-Cl—Ph | 8.20 ± 2.96 | 8.91 ± 0.97 | 0.0134 ± 0.0015 | 610 |
| 52 | $CH_2CH_3$ | $SCH_2CH_3$ | $CH_2CH_3$ | $CH_2CH_3$ | cyclopentyl | 55.3 ± 14.7 | 26.1 ± 6.2 | 4.01 ± 2.49 | 14 |
| 53 | $CH_2CH_3$ | $SCH_2CH_2CH_3$ | $CH_2CH_3$ | $CH_2CH_3$ | Ph | 8.22 ± 1.21 | 15.7 ± 4.4 | 0.0159 ± 0.0054 | 520 |
| 54 | $CH_2CH_3$ | $SCH_2CH_2CH_3$ | $CH_2CH_3$ | $CH_2CH_3$ | 3-Cl—Ph | 41.4 ± 11.9 | 24.1 ± 7.9 | 0.00242 ± 0.00070 | 17,000 |
| 55 | $CH_2CH_2CH_3$ | $SCH_2CH_3$ | $CH_2CH_3$ | $CH_2CH_3$ | Ph | 16.7 ± 3.0 | 2.82 ± 0.82 | 0.0333 ± 0.0107 | 500 |
| 56 | $(CH_2)_2OCH_3$ | $SCH_2CH_3$ | $CH_2CH_3$ | $CH_2CH_3$ | Ph | 10.1 ± 2.1 | 12.6 ± 1.7 | 0.0168 ± 0.0020 | 600 |
| 57 | $(CH_2)_3CH_3$ | $SCH_2CH_3$ | $CH_2CH_3$ | $CH_2CH_3$ | Ph | 40.3 ± 7.4 | d ($10^{-4}$) | 0.0350 ± 0.0091 | 1200 |
| 58 | cyclobutyl | $SCH_2CH_3$ | $CH_2CH_3$ | $CH_2CH_3$ | Ph | 30% ($10^{-4}$) | 22% ($10^{-4}$) | 0.145 ± 0.044 | >500 |

Figure 12:
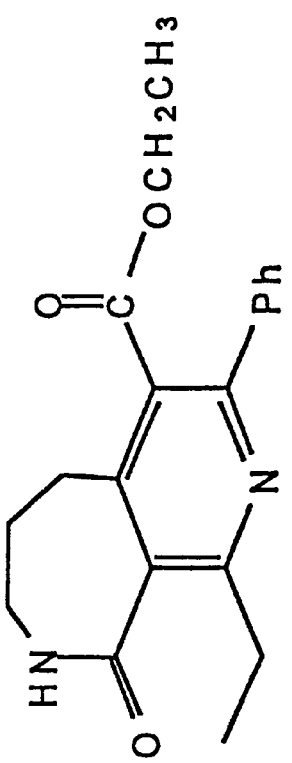
FIG. 12 depicts the formulas of pyridine derivatives 29–32.
Figure 12:
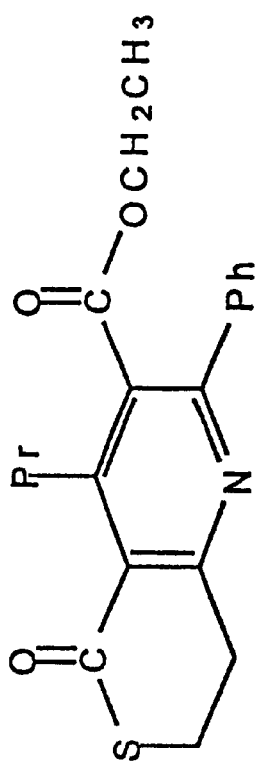
Figure 12:
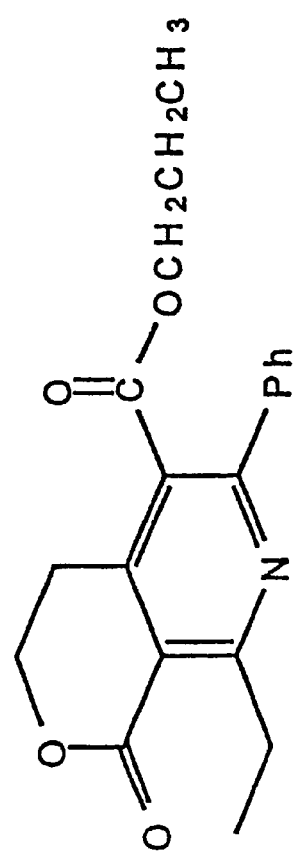
Figure 12:
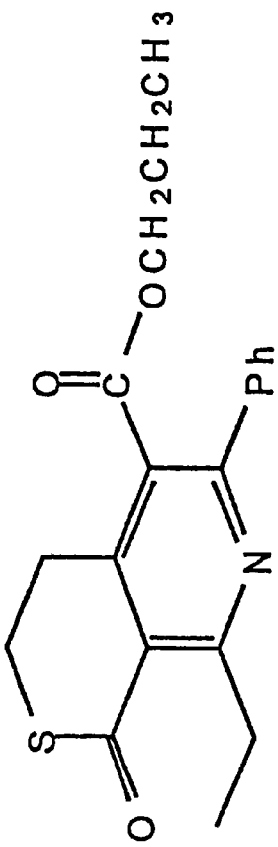
Figure 13:
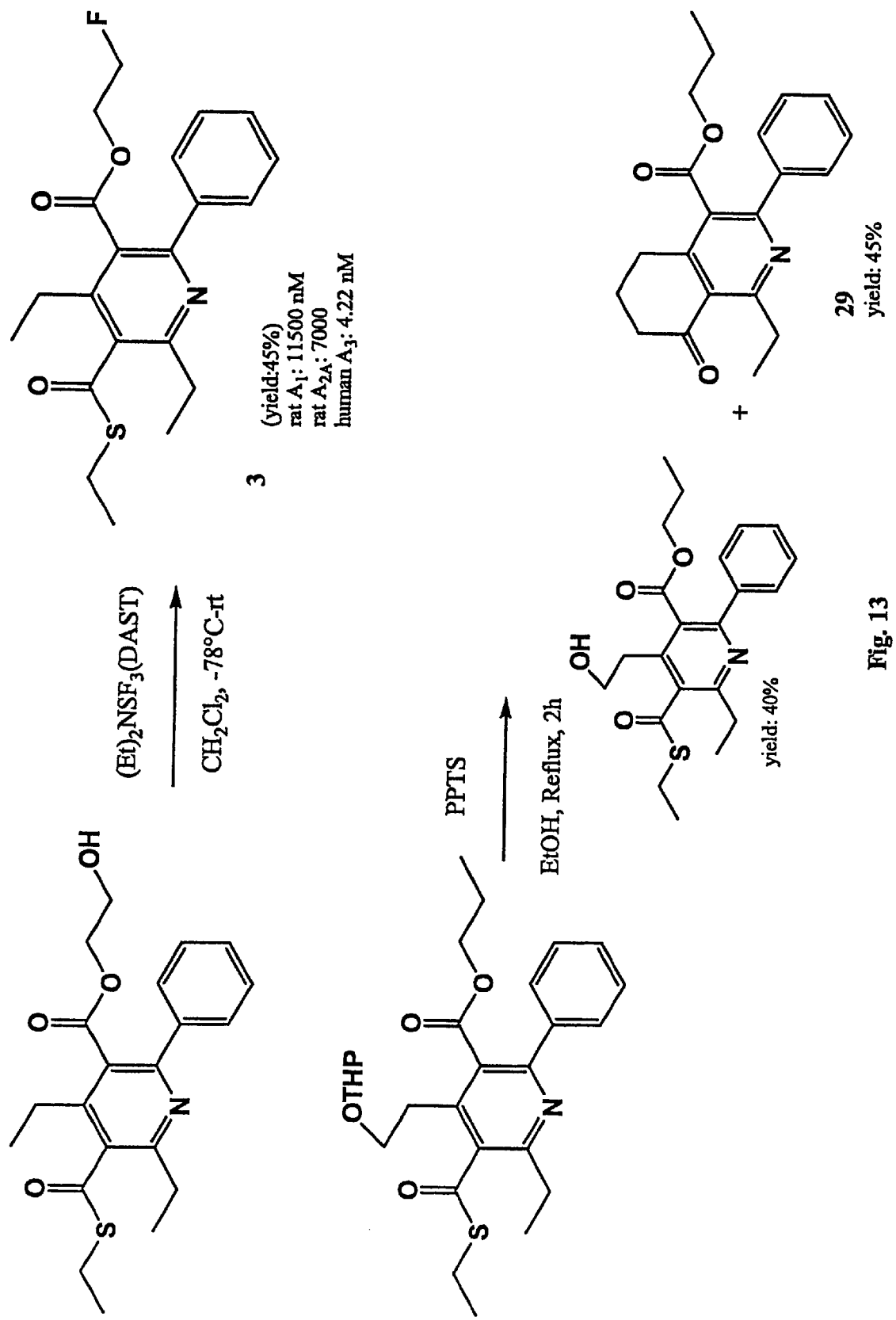
FIG. 13 depicts a method of synthesis of pyriding derivatives 3 and 29.
Figure 14:
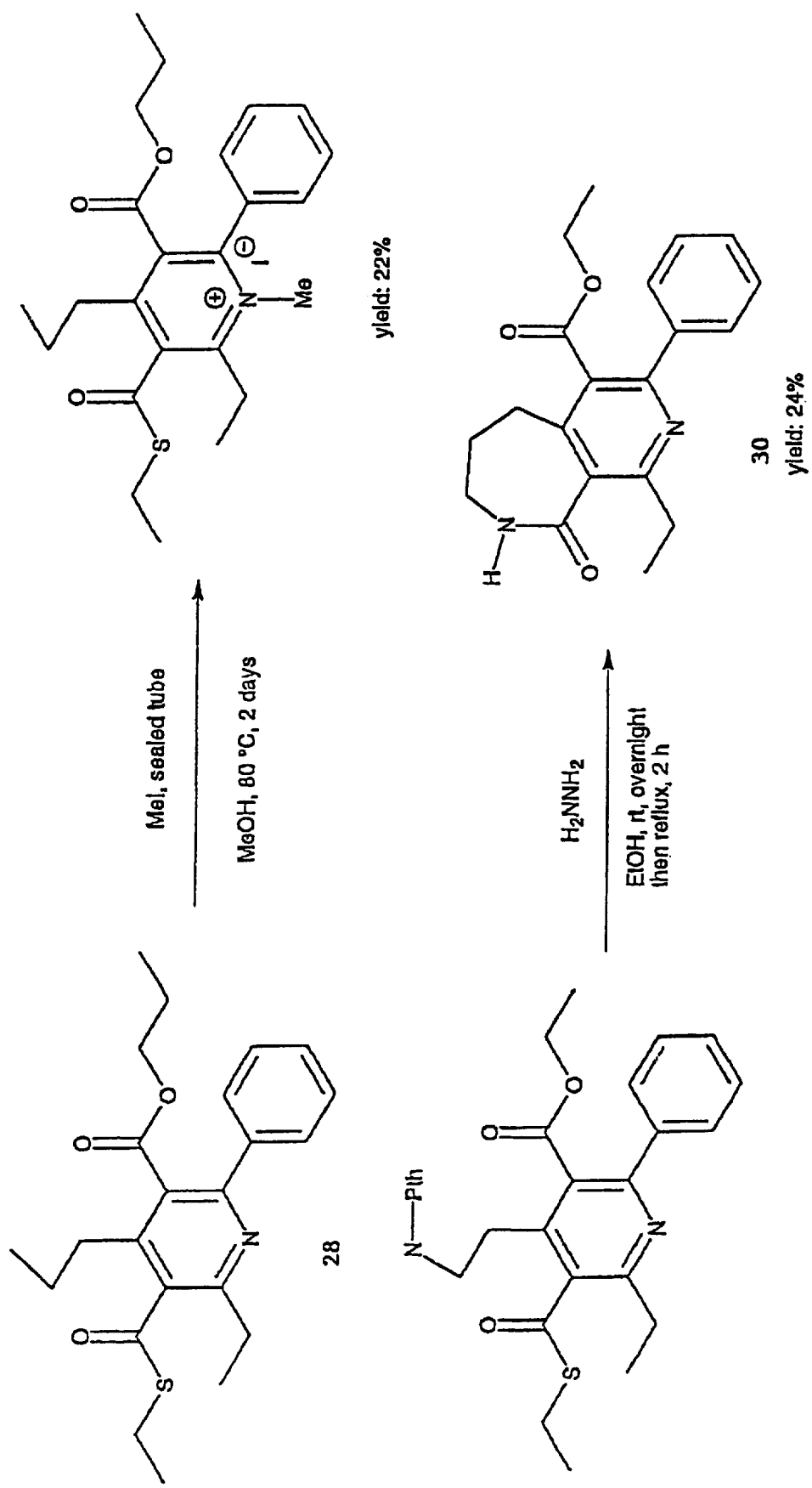
FIG. 14 depicts a method of synthesis of the pyridine derivative 30 and the N-1 methyl pyridinium salt of pyridine derivative 28.
Figure 15:
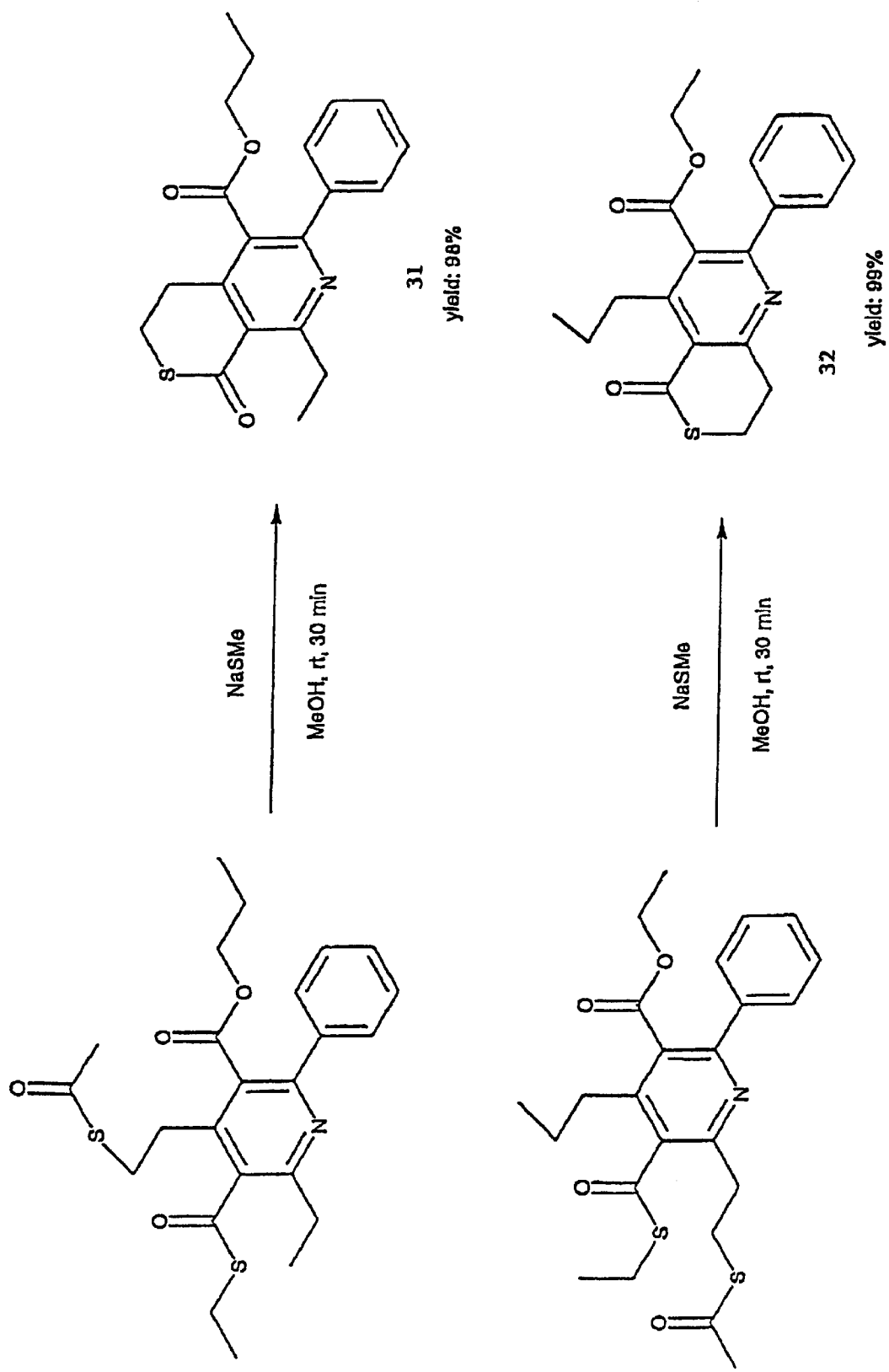
FIG. 15 depicts a method of synthesis of pyrdine derivatives 31–32.
Figure 16:
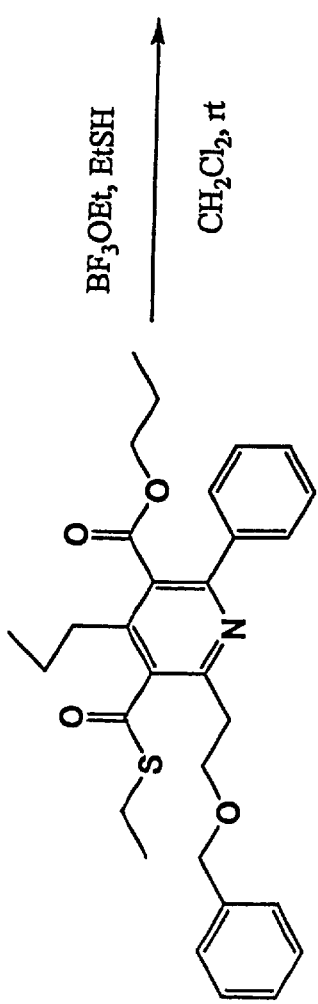
FIG. 16 depicts a method of synthesis of pyridine derivatives 8 and 10.
Figure 16:
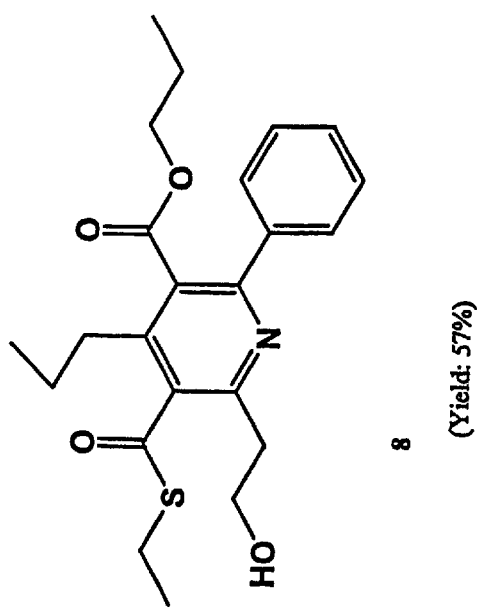
Figure 16:
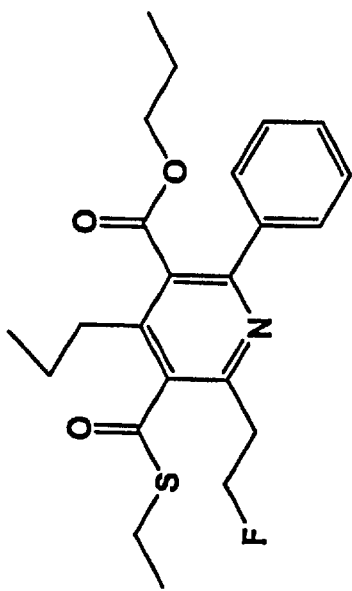
Figure 17:
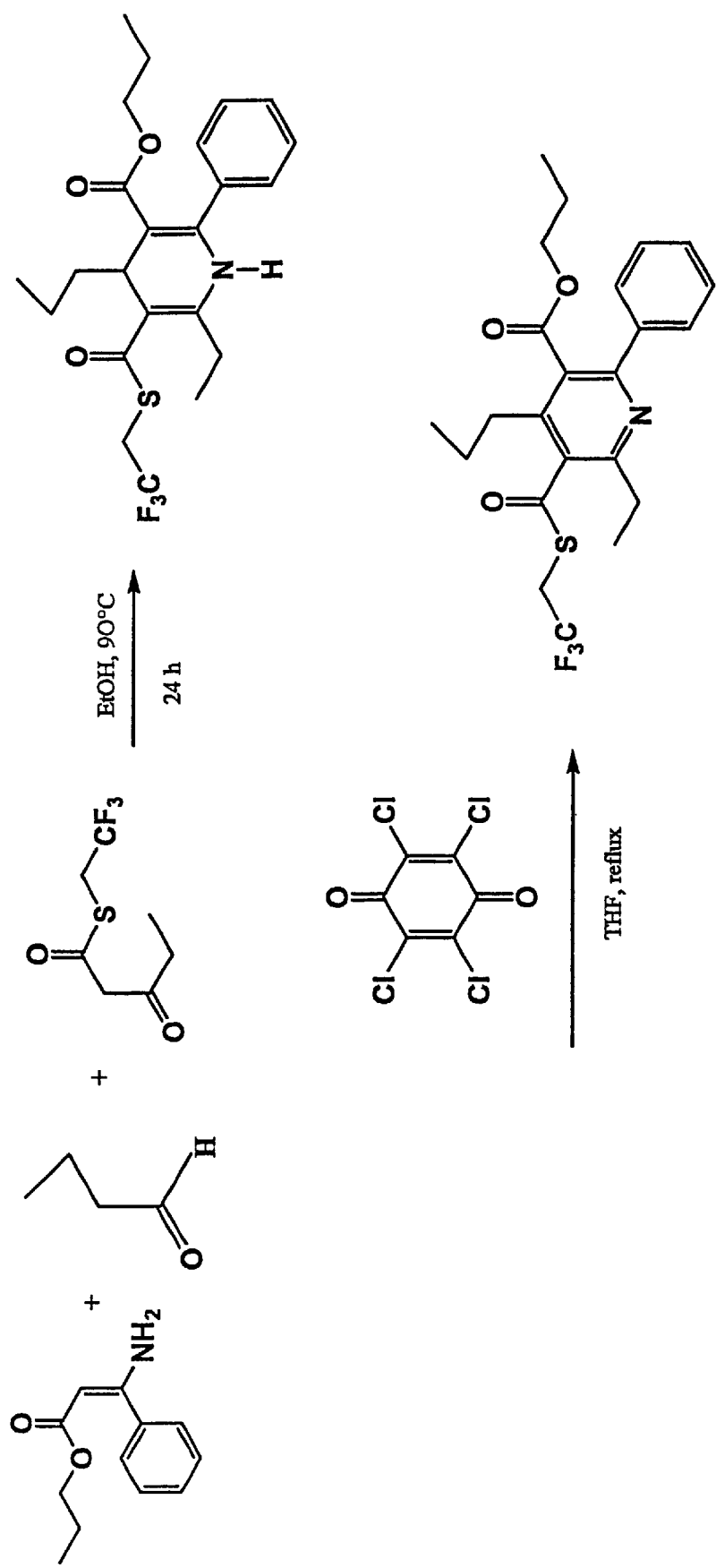
FIG. 17 depicts a method of synthesis of pyridine derivative 16.

[a]Displacement of specific [$^3$H]R - PIA binding in rat brain membranes, expressed as $K_i$ ± S.E.M. in $\mu M$ (n = 3–5), or as a percentage of specific binding displaced at the indicated concentration (M).
[b]Displacement of specific [$^3$H]CGS 21680 binding in rat striatal membranes, expressed as $K_i$ ± S.E.M. in $\mu M$ (n = 3–6), or as a percentage of specific binding displaced at the indicated concentration (M).
[c]Displacement of specific [$^{125}$I]AB-MECA binding at human $A_3$ receptors expressed in HEK cells, in membranes, expressed as $K_i$ ± S.E.M. in $\mu M$ (n = 3–4).
[d]Displacement of <10% of specific binding at the indicated concentration (M).
[e]Formulas of these compounds are set forth in FIG. 12.
[f]N-1 methyl pyridinium salt

EXAMPLE 12

This Example illustrates the $A_1$, $A_2$, and $A_3$ adenosine receptor binding affinities of certain dihydropyridine derivatives of the present invention. The affinities were determined in radioligand binding assays, and the results thereof are set forth in Table 3.

TABLE 3

Affinities of 1,4-dihydropyridine derivatives in radioligand binding assays at $A_1$, $A_{2A}$, and $A_3$ adenosine receptors

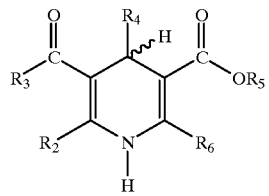

| | | | | | | $K_i$ ($\mu M$) or % inhibition[d] | | | |
|---|---|---|---|---|---|---|---|---|---|
| Compound | $R_2$ | $R_3$ | $R_4$ | $R_5$ | $R_6$ | $rA_1$[a] | $rA_{2A}$[b] | $hA_3$[c] | $rA_1/hA_3$ |
| 59[a] | $CH_3$ | $OCH_2CH_2$ | $CH_3$ | $CH_2CH_3$ | Ph | 25.9 ± 7.3 | 35.9 ± 15.3 | 7.24 ± 2.13 | 3.6 |
| 60 | $CH_3$ | $OCH_2CH_2CH_3$ | $CH_3$ | $CH_2CH_3$ | Ph | 1.74 ± 3.1 | 28.9 ± 4.8 | 2.11 ± 0.35 | 8.2 |
| 61 | $CH_3$ | $OCH_2CH_3$ | $CH_2CH_3$ | $CH_2CH_3$ | Ph | 21.9 ± 3.3 | 21.8 ± 7.8 | 2.27 ± 0.64 | 9.6 |
| 62 | $CH_3$ | $SCH_2CH_3$ | $CH_2CH_3$ | $CH_2CH_3$ | Ph | 35.4 ± 4.5 | 54.8 ± 18.8 | 2.01 ± 0.55 | 18 |
| 63 | $CH_3$ | $SCH_2CH_2OCH_3$ | $CH_2CH_3$ | $CH_2CH_3$ | Ph | 36 ± 14% ($10^{-4}$) | 12.5 ± 2.5 | 4.58 ± 0.35 | >10 |
| 64 | $CH_3$ | $SCH_2CH_3$ | $CH_2CH_2CH_3$ | $CH_2CH_3$ | Ph | 48 ± 5% ($10^{-4}$) | 29 ± 10% ($10^{-4}$) | 2.17 ± 0.25 | >20 |
| 65 | $CH_3$ | $SCH_2CH_3$ | $CH_2CH_3$ | $CH_2Ph$ | Ph | 45 ± 2% ($10^{-4}$) | 14.3 ± 4.2 | 1.65 ± 0.40 | >50 |
| 66 | $CH_3$ | $OCH_2CH_3$ | $CH(OCH_3)_2$ | $CH_2CH_3$ | Ph | 32 ± 5% ($10^{-4}$) | d ($10^{-4}$) | 15.3 ± 3.9 | >5 |
| 67 | $CH_3$ | $OCH_2CH_3$ | CHO | $CH_2CH_3$ | Ph | 26 ± 6% ($10^{-4}$) | 32 ± 15% ($10^{-4}$) | 15.6 ± 5.4 | >6 |
| 68[a] | $CH_3$ | $OCH_2CH_3$ | Ph—CH=CH— (trans) | $CH_2CH_3$ | Ph | 5.93 ± 0.27 | 4.77 ± 0.29 | 0.108 ± 0.012 | 55 |
| 69[a] | $CH_3$ | $OCH_2CH_3$ | Ph—C≡C— | $CH_2Ph$ | Ph | 40.1 ± 7.5 | d ($10^{-4}$) | 0.0314 ± 0.0028[f] | 1300 |
| 70 | $CH_3$ | $OCH_2CH_3$ | Ph—C≡C— | $CH_2Ph$ | cyclopropyl | 22 ± 1% ($10^{-4}$) | d ($10^{-4}$) | 0.0277 ± 0.0024 | >3000 |
| 71 | $CH_3$ | $OCH_2CH_3$ | Ph—C≡C— | $CH_2Ph$ | cyclobutyl | 36 ± 8% ($10^{-4}$) | d ($10^{-4}$) | 0.0225 ± 0.0030 | >3000 |
| 72 | $CH_3$ | $OCH_2CH_3$ | Ph—C≡C— | $CH_2Ph$ | cyclopentyl | 17.1 ± 4.3 | 7.16 ± 1.56 | 0.0505 ± 0.0210 | 340 |
| 73 | $CH_3$ | $OCH_2CH_3$ | Ph—C≡C— | $CH_2Ph$ | cyclohexyl | 22 ± 2% ($10^{-4}$) | 20% ($10^{-4}$) | 0.229 ± 0.014 | >400 |
| 74 | $CH_2CH_3$ | $OCH_2CH_3$ | $CH_3$ | $CH_2CH_3$ | Ph | 20 ± 4% ($10^{-4}$) | d ($10^{-4}$) | 2.83 ± 0.20 | >30 |
| 75 | $CH_2CH_3$ | $SCH_2CH_3$ | $CH_2CH_3$ | $CH_2CH_3$ | Ph | 34 ± 7% ($10^{-4}$) | 29.1 ± 9.9 | 0.907 ± 0.044 | >50 |
| 76 | $CH_2CH_2CH_3$ | $SCH_2CH_3$ | $CH_2CH_3$ | $CH_2CH_3$ | Ph | 26 ± 19% ($10^{-4}$) | d ($10^{-4}$) | 2.09 ± 0.04 | >20 |

[a]Displacement of specific [$^3$H]R - PIA binding in rat brain membranes, expressed as $K_i$ ± S.E.M. in $\mu M$ (n = 3–5), or as a percentage of specific binding displaced at the indicated concentration (M).

[b]Displacement of specific [$^3$H]CGS 21680 binding in rat striatal membranes, expressed as $K_i$ ± S.E.M. in $\mu M$ (n = 3–6), or as a percentage of specific binding displaced at the indicated concentration (M).

[c]Displacement of specific [$^{125}$I]AB-MECA binding at human $A_3$ receptors expressed in HEK cells, in membranes expressed as $K_i$ ± S.E.M. in $\mu M$ (n = 3–4).

[d]Displacement of < 10% of specific binding at the indicated concentration (M).

[e]Values taken from A.M. van Rhee et al., J.Med.Chem.,39, 2980–2989 (1996), and Jiang et al., J.Med.Chem.,40, 2596–2608 (1997)

EXAMPLE 13

This Example illustrates the binding affinities of certain dihydropyridines and pyridine derivatives of the present invention at rat $A_1$ and $A_3$ adenosine receptors. The results obtained are set forth in Table 4, along with the ratio of affinities at rat vs. human $A_3$ receptors. It was found that affinity at rat $A_3$ adenosine receptors was generally lower than at human $A_3$ receptors. Certain compounds, for example, 49b, displayed high affinity at both species.

TABLE 4

Affinities of certain dihydropyridine and pyridine derivatives in radioligand binding assays at rat $A_3$ receptors, and comparison to rat $A_1$ and human $A_3$ adenosine receptor affinities.

| Compound | $rA_3^a$ $K_i$ ($\mu$M) | $rA_1/rA_3$ | $rA_3/hA_3$ |
|---|---|---|---|
| 69 | 1.42 ± 0.19 | 28 | 45 |
| 62 | 4.60 ± 0.38 | 7.7 | 2.3 |
| 64 | 3.10 ± 0.78 | >20 | 1.4 |
| 65 | 2.80 ± 0.28 | >20 | 1.7 |
| 71 | 1.75 ± 0.18 | >40 | 78 |
| 75 | 2.52 ± 0.88 | >30 | 2.8 |
| 76 | 2.73 ± 0.14 | >30 | 1.3 |
| 36 | 1.47 ± 0.34 | 10 | 34 |
| 38 | 0.650 ± 0.070 | >100 | 3.4 |
| 39 | 1.80 ± 0.32 | >50 | 0.69 |
| 44 | 1.90 ± 0.42 | >50 | 0.79 |
| 48 | 0.410 ± 0.048 | >100 | 21 |
| 49a | 0.183 ± 0.033 | 42 | 22 |
| 49b | 0.113 ± 0.012 | 140 | 6.0 |
| 50 | 2.87 ± 0.48 | 6.1 | 15 |
| 51 | 0.440 ± 0.033 | 19 | 33 |
| 52 | 2.80 ± 0.22 | >20 | 0.83 |
| 53 | 0.294 ± 0.006 | 28 | 18 |
| 54 | 0.814 ± 0.037 | 50 | 100 |
| 55 | 0.590 ± 0.040 | 28 | 18 |
| 57 | 2.26 ± 0.05 | 18 | 64 |

[a]Displacement of specific [$^{125}$I]AB-MECA binding at rat $A_3$ receptors stably expressed in CHO cells (n = 3 – 5).

All of the references cited herein including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of the formula

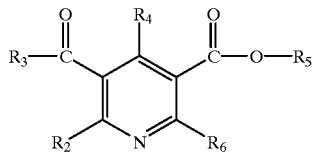

or a pharmaceutically acceptable salt thereof; wherein $R_2$ is selected from the group consisting of $C_1$–$C_6$ alkyl, $C_3$–$C_7$ cycloalkyl, and $C_1$–$C_6$ alkoxy $C_1$–$C_6$ alkyl; $R_3$ is selected from the group consisting of $C_1$–$C_6$ alkylsulfanyl, hydroxy, $C_1$–$C_6$ alkoxy $C_1$–$C_6$ alkylsulfanyl, hydroxy $C_1$–$C_6$ alkylsulfanyl, and halo $C_1$–$C_6$ alkylsulfanyl, or $R_3$ together with $R_4$ forms a 3–7 membered heterocyclic ring containing O, N, or S; $R_4$ is selected from the group consisting of $C_1$–$C_6$ alkyl, halo $C_1$–$C_6$ alkyl, hydroxy $C_1$–$C_6$ alkyl, $C_1$–$C_6$ alkoxy, $C_1$–$C_6$ alkylsulfanyl, $C_1$–$C_6$ alkylamino, $C_1$–$C_6$ alkylcarbonyl sulfanyl $C_1$–$C_6$ alkyl, aryl $C_2$–$C_6$ alkenyl, aryl $C_2$–$C_6$ alkynyl, formyl, and acetal; $R_5$ is selected from the group consisting of $C_1$–$C_6$ alkyl, aryl $C_1$–$C_6$ alkyl, hydroxy $C_1$–$C_6$ alkyl, and halo $C_1$–$C_6$ alkyl; and $R_6$ is selected from the group consisting of aryl, $C_3$–$C_7$ cycloalkyl, and haloaryl; wherein said aryl is a phenyl or naphthyl.

2. The compound of claim 1, wherein $R_2$ is selected from the group consisting of $C_1$–$C_4$ alkyl, $C_4$–$C_5$ cycloalkyl, and $C_1$–$C_3$ alkoxy $C_1$–$C_3$ alkyl; $R_3$ is selected from the group consisting of $C_1$–$C_6$ alkylsulfanyl, hydroxy $C_1$–$C_3$ alkylsulfanyl, and halo $C_1$–$C_3$ alkylsulfanyl; $R_4$ is selected from the group consising of $C_1$–$C_3$ alkyl and hydroxy $C_1$–$C_3$ alkyl; $R_5$ is selected from the group consisting of $C_1$–$C_3$ alkyl and halo $C_1$–$C_3$ alkyl; and $R_6$ is selected from the group consisting of $C_4$–$C_6$ cycloalkyl, phenyl, and halophenyl; or a pharmaceutically acceptable salt thereof.

3. The compound of claim 2, wherein $R_2$ is ethyl; $R_3$ is selected from the group consisting of $C_1$–$C_6$ alkylsulfanyl, hydroxy $C_1$–$C_2$ alkylsulfanyl, and halo $C_1$–$C_2$ alkylsulfanyl; $R_4$ is selected from the group consisting of $C_1$–$C_3$ alkyl and hydroxy $C_1$–$C_3$ alkyl; $R_5$ is selected from the group consisting of $C_1$–$C_3$ alkyl and halo $C_1$–$C_3$ alkyl; and $R_6$ is selected from the group consisting of phenyl and halophenyl; or a pharmaceutically acceptable salt thereof.

4. The compound of claim 3, wherein $R_2$ is ethyl; $R_3$ is selected from the group consisting of ethylsulfanyl, hexylsulfanyl, haloethylsulfanyl, and hydroxyethyl sulfanyl; $R_4$ is selected from the group consisting of ethyl, propyl, and hydroxypropyl; $R_5$ is selected from the group consisting of ethyl, propyl, fluoroethyl, and fluoropropyl; and $R_6$ is selected from the group consisting of phenyl and halophenyl; or a pharmaceutically acceptable salt thereof.

5. The compound of claim 4, wherein $R_2$ is ethyl; $R_3$ is ethylsulfanyl; $R_4$ is selected from the group consisting of ethyl propyl, and hydroxypropyl; $R_5$ is selected from the group consisting of ethyl, propyl, fluoroethyl, and fluoropropyl; and $R_6$ is phenyl or fluorophenyl; or a pharmaceutically acceptable salt thereof.

6. The compound of claim 5, wherein said compound is selected from the group consisting of 5-ethyl 2,4-diethyl 3-(ethylsulfanylcarbonyl)-6-phenylpyridine-5-carboxylate, 5-(2-fluoroethyl)-2,4-diethyl-3-(ethylsulfanylcarbonyl)-6-phenylpyridine-5-carboxylate, 5-n-propyl 2,4-diethyl-3-(ethylsulfanylcarbonyl)-6-phenylpyridine-5-carboxylate, 5-n-propyl 2-ethyl-4-n-propyl-3-(ethylsulfanylcarbonyl)-6-phenylpyridine-5-carboxylate, 5-n-propyl-2-ethyl-4-(3-hydroxy-n-propyl)-3-(ethylsulfanylcarbonyl)-6-phenylpyridine-5-carboxylate 5-(3-fluoro-n-propyl) 2-ethyl-4-n-propyl-3-ethylsulfanylcarbonyl)-6-phenylpyridine-5-carboxylate, 5-n-propyl 2-ethyl-4-n-propyl-3-(ethylsulfanylcarbonyl)-6-(2-fluorophenyl)pyridine-5-carboxylate, 5-n-propyl 2-ethyl-4-n-propyl-3-(ethylsulfanylcarbonyl)-6-(3-fluorophenyl) pyridine-5-carboxylate, and 5-n-propyl 2-ethyl-4 -n-propyl-3-(ethylsulfanylcarbonyl)-6-(4-fluorophenyl) pyridine-5-carboxylate; or a pharmaceutically acceptable salt thereof.

7. The compound of claim 4, wherein $R_2$ is ethyl; $R_3$ is selected from the group consisting of hexylsulfanyl, haloethylsulfanyl and hydroxyethylsulfanyl; $R_4$ is selected from the group consisting of ethyl and propyl; $R_5$ is propyl; and $R_6$ is phenyl; or a pharmaceutically acceptable salt thereof.

8. The compound of claim 7, wherein said compound is selected from the group consisting of 5-n-propyl 2,4-diethyl-3-(n-hexylsulfanylcarbonyl)-6-phenylpyridine-5-carboxylate, 5-n-propyl 2-ethyl-4-n-propyl-3-(2- hydroxyethylsulfanylcarbonyl)-6-phenylpyridine-5-carboxylate, 5-n-propyl 2-ethyl-4-n-propyl-3-(2-fluoroethylsulfanylcarbonyl)-6-phenyl pyridine-5-carboxylate, and 5-n-propyl 2-ethyl-4-n-propyl-3-(2,2,2-trifluoroethylsulfanylcarbonyl)-6-phenylpyridine-5-carboxylate; or a pharmaceutically acceptable salt thereof.

9. A compound of the formula

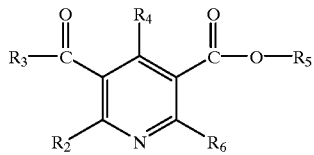

or a pharmaceutically acceptable salt thereof; wherein $R_2$ is methyl; $R_3$ is selected from the group consisting of ethylsulfanyl, and methoxyethylsulfanyl; $R_4$ is selected from the group consisting of $C_1$–$C_3$ allyl and phenyl acetylenyl; $R_5$ is selected from the group consisting ethyl and benzyl; and $R_6$ is selected from the group consisting of phenyl and $C_3$–$C_5$ cycloalkyl; or a pharmaceutically acceptable salt thereof.

10. A compound of the formula

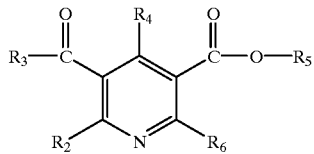

or a pharmaceutically acceptable salt thereof, wherein $R_2$ is methyl; $R_3$ is selected from the group consisting of $C_1$–$C_6$ alkoxy, ethylsulfanyl, and methoxyethylsulfanyl; $R_4$ is selected from the group consisting of $C_1$–$C_3$ alkyl and phenyl acetylenyl; $R_5$ is selected from the group consisting ethyl and benzyl; and $R_6$ is selected from the group consisting of $C_3$–$C_5$ cycloalkyl; or a pharmaceutically acceptable salt thereof.

11. A compound selected from the group consisting of 3-n-propyl 5-ethyl-2,4-dimethyl-6-phenylpyridine-3,5-dicarboxylate, 3,5-diethyl 2-methyl-4-ethyl-6-phenylpyridine-3,5-dicarboxylate, 5-ethyl 2-methyl-4ethyl-3-(ethylsulfanylcarbonyl)-6-phenylpyridine-5-carboxylate, 5-ethyl 2-methyl-4-n-propyl-3(ethylsulfanylcarbonyl)-6-phenylpyridine-5-carboxylate, 5-benzyl 2-methyl-4-ethyl-3-(ethylsulfanylcarbonyl)-6-phenylpyridine-5-carboxylate, 3-ethyl 5-benzyl-2-methyl-4-phenylethynyl-6-cyclobutylpyridine-3,5-dicarboxylate, 3-ethyl 5-benzyl-2-methyl-4-phenylethynyl-6-cyclopentylpyridine-3,5-dicarboxylate, 3-ethyl-5-benzyl-2-methyl-4-phenylethyl-6-phenylpyridine-3,5-dicarboxylate, 3,5-diethyl 2-methyl-4-(dimethoxymethyl)-6-phenylpyridine-3,5-dicarboxylate, and 3,5-diethyl 2-ethyl-4-methyl-6-phenylpyridine-3,5-dicarboxylate; or a pharmaceutically acceptable thereof.

12. The compound of claim 1, wherein $R_2$ is selected from the group consisting of ethyl, propyl, butyl, cyclobutyl, and methoxyethyl; $R_3$ is selected from the group consisting of ethylsulfanyl and propylsulfanyl; $R_4$ is selected from the group consisting of methyl, ethyl, and propyl; $R_5$ is selected from the group consisting of ethyl, propyl, and hydroxyethyl; and $R_6$ is selected from the group consisting of phenyl, chlorophenyl, and cyclopentyl; or a pharmaceutically acceptable salt thereof.

13. The compound of claim 12, wherein said compound is selected from the group consisting of 5-ethyl 2-diethyl-3-(ethylsulfanylcarbonyl)-6-phenylpyridine-5-carboxylate, 5-propyl 2,4-diethyl-3-(ethylsulfanylcarbonyl)-6-phenylpyridine-5-carboxylate, 5-propyl 2-ethyl-4-propyl-3-(ethylsulfanylcarbonyl)-6-phenylpyridine-5-carboxylate, 5-hydroxylethyl 2,4diethyl-3-(ethylsulfanylcarbonyl)-6-phenylpyridine-5-carboxylate, 5-ethyl 2,4-diethyl-3-(ethylsulfanylcarbonyl)-6-(m-chlorophenyl)pyridine-5-carboxylate, 5-ethyl 2,4-diethyl-3-(ethylsulfanylcarbonyl)-6-cyclopentylpyridine-5-carboxylate, 5-ethyl 2,4-diethyl-3-propylsulfanylcarbonyl-7-phenylpyridine-5-carboxylate, 5-propyl 2,4-diethyl-3-propylsulfanylcarbonyl-6-(m-chlorophenyl)pyridine-5-carboxylate, 5-ethyl 2-propyl-4-ethyl-3-(ethylsulfanylcarbonyl)-6-phenylpyridine-5-carboxylate, 5-ethyl 2-(2-methoxyethyl)-4-ethyl-3-(ethylsulfanylcarbonyl)-6-phenylpyridine-5-carboxylate, 5-ethyl 2-butyl-4-ethyl-3-(ethylsulfanylcarbonyl)-6-phenylpyridine-5-carboxylate, and 5-ethyl 2-cyclobutyl-4-ethyl-3-(ethylsulfanylcarbonyl)-6-phenylpyridine-5-carboxylate; or a pharmaceutically acceptable salt thereof.

14. A compound of the formula

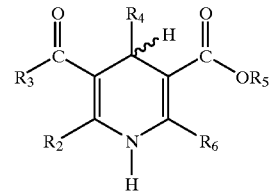

or a pharmaceutically acceptable salt thereof; wherein $R_2$ is a $C_1$–$C_6$ alkyl; $R_3$ is selected from the group consisting of $C_1$–$C_6$ alkoxy $C_1$–$C_6$ alkylsulfanyl and $C_1$–$C_6$ alkylsulfanyl; $R_4$ is selected from the group consisting of $C_1$–$C_6$ alkyl, acetal, formyl, aryl $C_2$–$C_6$ alkenyl, and aryl $C_2$–$C_6$ alkynyl; $R_5$ is selected from the group consisting of $C_1$–$C_6$ alkyl and aryl $C_1$–$C_6$ alkyl; and $R_6$ is selected from the group consisting of naphthyl and $C_3$–$C_6$ cycloalkyl.

15. The compound of claim 14, wherein $R_2$ is a $C_1$–$C_6$ alkyl; $R_3$ is selected from the group consisting of $C_1$–$C_6$ alkoxy $C_1$–$C_6$ alkylsulfanyl and $C_1$–$C_6$ alkylsulfanyl; $R_4$ is selected from the group consisting of $C_1$–$C_6$ alkyl, acetal, formyl, aryl $C_2$–$C_6$ alkenyl, and aryl $C_2$–$C_6$ alkynyl; $R_5$ is selected from the group consisting of $C_1$–$C_6$ alkyl and aryl $C_1$–$C_6$ alkyl; and $R_6$ is $C_3$–$C_6$ cycloalkyl; or a pharmaceutically acceptable salt thereof.

16. The compound of claim 14, wherein $R_2$ is a $C_1$–$C_6$ alkyl; $R_3$ is selected from the group consisting of $C_1$–$C_6$ alkoxy $C_1$–$C_6$ alkylsulfanyl, and $C_1$–$C_6$ alkylsulfanyl; $R_4$ is selected from the group consisting of $C_1$–$C_6$ alkyl, acetal, formyl, aryl $C_2$–$C_6$ alkenyl, and aryl $C_2$–$C_6$ alkynyl; $R_5$ is selected from the group consisting of $C_1$–$C_6$ alkyl and aryl $C_1$–$C_6$ alkyl; and $R_6$ is naphthyl; or a pharmaceutically acceptable salt thereof.

17. A compound selected from the group consisting of 3-ethyl 5-benzyl 2-methyl-4-phenylethynyl-6-cyclopropyl-1,4-(±)-dihydropyridine-3,5-dicarboxylate, 3-ethyl 5-benzyl 2-methyl-4-phenylethynyl-6-cyclobutyl-1,4-(±)-dihydropyridine-3,5-dicarboxylate, 3-ethyl 5-benzyl 2-methyl-4phenylethynyl-6-cyclopentyl-1,4-(±)-dihydropyridine-3,5-dicarboxylate, and 3-ethyl 5-benzyl 2-methyl-4 phenylethynyl-6-cyclohexyl-1,4-(±)-dihydropyridine-3,5-dicarboxylate; or a pharmaceutically acceptable salt thereof.

18. A compound selected from the group consisting of 3,5-diethyl 2,4-dimethyl-6-phenyl-1,4-(±)-dihydropyrdine-3,5-carboxylate, 3-propyl 5-ethyl-2,4dimethyl-6-phenyl-1, 4-(±)-dihydropyridine-3,5-dicarboxylate, 3,5-diethyl 2-methyl-4-ethyl-6-phenyl-1,4-(±)-dihydropyridine-3,5-dicarboxylate, 5-ethyl 2-methyl-4-ethyl-6-phenyl-3-(ethylsulfanylcarbonyl)-1,4-(±)-dihydropyridine-5-carboxylate, 5-ethyl 2-methyl-4-ethyl-6-phenyl-3-(2-methoxyethylsulfanylcarbonyl)-1,4-(±)-dihydropyridine-5-carboxylate, 5-ethyl 2-methyl-4-propyl-6-phenyl-3-(ethylsulfanylcarbonyl)-1,4-(±)-dihydropyridine-5-carboxylate, 5-benzyl 2-methyl-4-ethyl-6-phenyl-3-(ethylsulfanylcarbonyl)-1,4-(±)-dihydropyridine-5-carboxylate, 3,5-diethyl 2-methyl-6-phenyl-4-(dimethoxymethyl)-1,4-(±)-dihydropyridine-3,5-dicarboxylate, 3,5-diethyl 2-ethyl-6-phenyl-4-methyl-1,4-(±)-dihydropyridine-3,5-dicarboxylate, 5-ethyl 2,4-diethyl-6-phenyl-3-(ethylsulfanylcarbonyl)-1,4-(±)-dihydropyridine-5-carboxylate, and 5-ethyl 2-propyl-4-ethyl-6-phenyl-3-(ethylsulfanylcarbonyl)-1,4-(±)-dihydropyridine-5-carboxylate; or a pharmaceutically acceptable salt thereof.

19. A pharmaceutical composition comprising a compound of claim 1 and a pharmaceutically acceptable carrier.

20. A method of selectively blocking an $A_3$ adenosine receptor of a mammal comprising administering to said mammal a compound of claim 1.

21. The method of claim 20, wherein said compound acts as a cerebroprotectant in said mammal.

22. A method of inhibiting the binding of a ligand to an adenosine receptor of a substrate comprising contacting said substrate with a compound of claim 1 so that said compound binds to said adenosine receptor and inhibits said ligand from binding to said adenosine receptor.

23. The method of claim 22, wherein said contacting is carried out in vitro.

24. The method of claim 22, wherein said contacting is carried out in vivo.

25. A method of characterizing an adenosine receptor site in a substrate comprising contacting said substrate with a compound of claim 1 and evaluating the interaction of said compound and said adenosine receptor.

26. A pharmaceutical composition comprising a compound of claim 9 and a pharmaceutically acceptable carrier.

27. A pharmaceutical composition comprising a compound of claim 10 and a pharmaceutically acceptable carrier.

28. A pharmaceutical composition comprising a compound of claim 11 and a pharmaceutically acceptable carrier.

29. A pharmaceutical composition comprising a compound of claim 14 and a pharmaceutically acceptable carrier.

30. A pharmaceutical composition comprising a compound of claim 17 and a pharmaceutically acceptable carrier.

31. A pharmaceutical composition comprising a compound of claim 18 and a pharmaceutically acceptable carrier.

32. A method of selectively blocking an $A_3$ adenosine receptor of a mammal comprising administering to said mammal a compound of claim 9.

33. A method of selectively blocking an $A_3$ adenosine receptor of a mammal comprising administering to said mammal a compound of claim 10.

34. A method of selectively blocking an $A_3$ adenosine receptor of a mammal comprising administering to said mammal a compound of claim 11.

35. A method of selectively blocking an $A_3$ adenosine receptor of a mammal comprising administering to said mammal a compound of claim 14.

36. A method of selectively blocking an $A_3$ adenosine receptor of a mammal comprising administering to said mammal a compound of claim 17.

37. A method of selectively blocking an $A_3$ adenosine receptor of a mammal comprising administering to said mammal a compound of claim 18.

38. A method of inhibiting the binding of a ligand to an adenosine receptor of a substrate comprising contacting said substrate with a compound of claim 9 so that said compound binds to said adenosine receptor and inhibits said ligand from binding to said adenosine receptor.

39. A method of inhibiting the binding of a ligand to an adenosine receptor of a substrate comprising contacting said substrate with a compound of claim 10 so that said compound binds to said adenosine receptor and inhibits said ligand from binding to said adenosine receptor.

40. A method of characterizing an adenosine receptor site in a substrate comprising contacting said substrate with a compound of claim 9 and evaluating the interaction of said compound and said adenosine receptor.

* * * * *